(12) United States Patent
Koike et al.

(10) Patent No.: US 12,398,382 B2
(45) Date of Patent: Aug. 26, 2025

(54) SOLUBLE EXPRESSION OF PROTEIN USING PEPTIDE TAG

(71) Applicant: IDEMITSU KOSAN CO., LTD., Chiyoda-ku (JP)

(72) Inventors: Kazuyoshi Koike, Sodegaura (JP); Eiji Takita, Sodegaura (JP); Takeshi Matsui, Sodegaura (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 759 days.

(21) Appl. No.: 17/271,960

(22) PCT Filed: Aug. 28, 2019

(86) PCT No.: PCT/JP2019/033792
§ 371 (c)(1),
(2) Date: Feb. 26, 2021

(87) PCT Pub. No.: WO2020/045530
PCT Pub. Date: Mar. 5, 2020

(65) Prior Publication Data
US 2022/0275353 A1    Sep. 1, 2022

(30) Foreign Application Priority Data
Aug. 31, 2018 (JP) .................. 2018-163783

(51) Int. Cl.
*C12N 9/16* (2006.01)
*C12P 21/02* (2006.01)

(52) U.S. Cl.
CPC ............... *C12N 9/16* (2013.01); *C12P 21/02* (2013.01); *C12Y 301/01003* (2013.01); *C07K 2319/02* (2013.01); *C07K 2319/21* (2013.01)

(58) Field of Classification Search
CPC ... C12N 9/16; C12P 21/02; C12Y 301/01003; C07K 2319/02; C07K 2319/21
See application file for complete search history.

(56) References Cited

U.S. PATENT DOCUMENTS

| | | |
|---|---|---|
| 2009/0137004 A1 | 5/2009 | Uversky et al. |
| 2011/0231960 A1 | 9/2011 | Sawada et al. |
| 2019/0024094 A1 | 1/2019 | Koike et al. |

FOREIGN PATENT DOCUMENTS

| | | | |
|---|---|---|---|
| WO | WO 2009/133882 A1 | 11/2009 | |
| WO | WO-2017115853 A1 * | 7/2017 | ............. C07K 14/00 |

(Continued)

OTHER PUBLICATIONS

Partial Supplementary European Search Report issued May 11, 2022 in European Patent Application No. 19853479.4, 16 pages.
(Continued)

*Primary Examiner* — Thomas J. Visone
*Assistant Examiner* — Georgiana C Reglas
(74) *Attorney, Agent, or Firm* — Oblon, McClelland, Maier & Neustadt, L.L.P.

(57) ABSTRACT

By linking a peptide tag having the amino acid sequence $X(PY)_qPZ$ to a protein of interest, and then expressing the protein, the protein of interest is efficiently accumulated in a soluble fraction, where P is proline; X is an amino acid sequence composed of 0 to 5 amino acids independently selected from R, G, S, K, T, L, N, Q, and M; Y is an amino acid sequence composed of 1 to 4 amino acids independently selected from R, G, K, T, L, N, Q, and M; q is an integer 1 to 10; and Z is an amino acid sequence composed of 0 to 10 amino acids independently selected from R, G, S, (Continued)

K, T, L, N, Q, and M; where the amino acid sequence of the peptide tag contains three or more Qs, Ms, Ls, Ns, and/or Ts in total.

8 Claims, 4 Drawing Sheets

Specification includes a Sequence Listing.

(56) References Cited

FOREIGN PATENT DOCUMENTS

| | | |
|---|---|---|
| WO | WO 2017/217460 A1 | 12/2017 |
| WO | WO 2019/167962 A1 | 9/2019 |

OTHER PUBLICATIONS

Database Genseq [Online] GSO:BEC45870, Jul. 6, 2017, XP55916634, 1 page.
Database Geneseq, [Online] GSP:BEC45872, Aug. 24, 2017, XP55916623, 1 page.
Wu, D., et al., "High-level secretory expression of metchinikowin in *Escherichia coli*", Protein Expression and Purification, vol. 91, 2013, pp. 49-53.
International Search Report issued Nov. 19, 2019 in PCT/JP2019/033792 filed Aug. 28, 2019, 2 pages.

* cited by examiner

SOLUBLE EXPRESSION OF PROTEIN USING PEPTIDE TAG

REFERENCE TO A SEQUENCE LISTING

In accordance with 37 CFR § 1.831-1835 and 37 CFR § 1.77 (b) (5), the specification makes reference to a Sequence Listing submitted electronically as a .txt file named "535637US_012822.txt". This .txt file was generated on Jan. 28, 2022 and is 56,004 bytes in size. The Sequence Listing is already of record and has a USPTO Filing/Load Date according to Patent Center of Mar. 14, 2022. The entire contents of the Sequence Listing are hereby incorporated by reference.

TECHNICAL FIELD

The present invention relates to a technology for producing a recombinant protein, more specifically, a technology for allowing efficient expression of a recombinant protein in a soluble fraction.

BACKGROUND ART

Advancement of the gene recombination technique has enabled heterologous expression of useful proteins derived from higher organisms, utilizing *E. coli*, yeast, or the like. Such advancement, today, has rendered production of useful proteins by heterologous expression available as a common technique. For improvement of expression of useful proteins and their amounts accumulated, studies have been carried out in relation to selection of promoters and terminators, utilization of translational enhancers, codon modification of transgenes, intracellular transport and localization of proteins, and the like. In some other techniques that have been developed, expression of a useful protein is improved by linking a peptide tag thereto. For example, Patent Document 1 discloses that, by linking an ENTROPIC BRISTLE DOMAIN (EBD) peptide to a useful protein, and then expressing the resulting protein, improved expression of the useful protein in a soluble fraction can be achieved. However, since the EBD peptide contains serine between prolines, total protein production may be low.

PRIOR ART DOCUMENT

Patent Document

[Patent Document 1] US20090137004 A

SUMMARY OF THE INVENTION

Problems to be Solved by the Invention

An object of the present invention is to allow efficient production of a protein of interest in a soluble fraction, in the recombination protein production technique.

Means for Solving the Problems

In order to solve the above problem, the present inventors intensively studied. As a result, the present inventors found that use of a peptide tag having the amino acid sequence shown below enables remarkable improvement of the expression level of a protein of interest in a soluble fraction. More specifically, by intensively modifying the amino acid composition and the sequence of the peptide tag to be linked, the expression level of the protein of interest in the soluble fraction was successfully and dramatically improved while the expression level of the protein of interest was maintained. The present invention was completed based on such findings.

The present invention can be summarized as follows.

[1] A soluble fraction prepared by an expression system comprising a polynucleotide introduced therein, the polynucleotide encoding a fusion protein containing:
a protein of interest; and
a peptide tag linked to the protein of interest and containing the following amino acid sequence:

$X(PY)_qPZ$ wherein
P represents proline;
X represents an amino acid sequence composed of 0 to 5 amino acids independently selected from the group consisting of arginine (R), glycine (G), serine (S), lysine (K), threonine (T), leucine (L), asparagine (N), glutamine (Q), and methionine (M);
Y represents an amino acid sequence composed of 1 to 4 amino acids independently selected from the group consisting of R, G, K, T, L, N, Q, and M;
q represents an integer of 1 to 10; and
Z represents an amino acid sequence composed of 0 to 10 amino acids independently selected from the group consisting of R, G, S, K, T, L, N, Q, and M;
with the proviso that the amino acid sequence of the peptide tag contains three or more Q('s), M('s), L('s), N('s), and/or T('s) in total;
the soluble fraction comprising the fusion protein produced and accumulated from the polynucleotide.

[2] The soluble fraction according to [1], wherein PY is one or more selected from PGQ, PGM, PGT, PGL, PQQ, PGN, PGQG, PGMG, PGTG, PGLG, PGNG, and PQQQ.

[3] The soluble fraction according to [1] or [2], wherein the peptide tag has a length of 10 to 30 amino acids.

[4] The soluble fraction according to any one of [1] to [3], wherein the peptide tag has the amino acid sequence of SEQ ID NO:7, 10, 12, 15, 17, 19, 21, or 23.

[5] The soluble fraction according to any one of [1] to [4], wherein the protein of interest is an enzyme.

[6] The soluble fraction according to any one of [1] to [5], wherein the fusion protein contains a secretion signal.

[7] The soluble fraction according to any one of [1] to [6], wherein the peptide tag is linked to the C-terminal side of the protein of interest.

[8] A method of producing a fusion protein, the method comprising collecting the soluble fraction according to any one of [1] to [7], and extracting the fusion protein.

[9] An expression system comprising a polynucleotide introduced therein, the polynucleotide encoding a fusion protein containing:
a protein of interest; and
a peptide tag linked to the protein of interest and containing the following amino acid sequence:

$X(PY)_qPZ$ wherein
P represents proline;
X represents an amino acid sequence composed of 0 to 5 amino acids independently selected from the group consisting of arginine (R), glycine (G), serine (S), lysine (K), threonine (T), leucine (L), asparagine (N), glutamine (Q), and methionine (M);

Y represents an amino acid sequence composed of 1 to 4 amino acids independently selected from the group consisting of R, G, K, T, L, N, Q, and M;

q represents an integer of 1 to 10; and

Z represents an amino acid sequence composed of 0 to 10 amino acids independently selected from the group consisting of R, G, S, K, T, L, N, Q, and M;

with the proviso that the amino acid sequence of the peptide tag contains three or more Q('s), M('s), L('s), N('s), and/or T('s) in total;

wherein said expression system produces the fusion protein without denaturation.

[10] A solution containing the nondenatured fusion protein produced from the expression system according to [9].

[11] A method of increasing efficiency of material production by a metabolic system involving enzyme, the method comprising:

producing the fusion protein, whose protein of interest is an enzyme, as a nondenatured protein using the expression system according to [9]; and carrying out substrate conversion reaction using the resulting nondenatured enzyme fusion protein.

[12] A fusion protein comprising:

a protein of interest; and a peptide tag linked to the protein of interest and containing the following amino acid sequence:

X(PY)$_q$PZ wherein

P represents proline;

X represents an amino acid sequence composed of 0 to 5 amino acids independently selected from the group consisting of arginine (R), glycine (G), serine (S), lysine (K), threonine (T), leucine (L), asparagine (N), glutamine (Q), and methionine (M);

Y represents an amino acid sequence composed of 1 to 4 amino acids independently selected from the group consisting of R, G, K, T, L, N, Q, and M;

q represents an integer of 1 to 10; and

Z represents an amino acid sequence composed of 0 to 10 amino acids independently selected from the group consisting of R, G, S, K, T, L, N, Q, and M;

with the proviso that the amino acid sequence of the peptide tag contains three or more Q('s), M('s), L('s), N('s), and/or T('s) in total, and contains at least one M.

[13] The fusion protein according to [12], wherein PY is one or more selected from PGM and PGMG.

[14] The fusion protein according to or [13], wherein the peptide tag has a length of 10 to 30 amino acids.

[15] The fusion protein according to any one of to [14], wherein the peptide tag has the amino acid sequence of SEQ ID NO:7, 10, 12, 15, 17, 19, 21, or 23.

[16] The fusion protein according to any one of to [15], wherein the protein of interest is an enzyme.

[17] The fusion protein according to any one of to [15], wherein the fusion protein contains a secretion signal.

[18] The fusion protein according to any one of to [17], wherein the peptide tag is linked to the C-terminal side of the protein of interest.

[19] A polynucleotide encoding the fusion protein according to any one of to [18].

[20] A recombinant vector comprising the polynucleotide according to [19].

Effect of the Invention

According to the present invention, linking of a peptide tag containing a particular sequence enables improvement of the expression efficiency of a protein of interest and improvement of the amount of the protein accumulated in a soluble fraction, so that separation and purification of the protein of interest can be easily carried out. In cases where the protein of interest contains a secretion signal sequence, the efficiency of secretory production of the protein of interest into the medium can also be improved.

In cases where the protein of interest is an enzyme, a solution containing a nondenatured enzyme fusion protein can be easily prepared from a medium, cell homogenate, or the like, and can be applied to enzymatic reaction by a metabolic system involving the enzyme, so that the enzyme can contribute to material production utilizing an efficient conversion reaction of a substrate.

Moreover, since the enzyme introduced is less likely to aggregate or to become insoluble in the cell, the enzyme can efficiently contribute also to intracellular enzymatic reaction.

Unlike the peptide tag described in Patent Document 1, the peptide tag to be used in the present invention does not contain serine between prolines. Thus, the peptide tag to be used in the present invention can be expected to improve production of the protein in a soluble fraction. The improvement of expression of the fusion protein in the soluble fraction can be achieved also in cases where the peptide tag is linked to the C-terminal side of the protein of interest.

EMBODIMENTS FOR CARRYING OUT THE INVENTION

Figure 1:
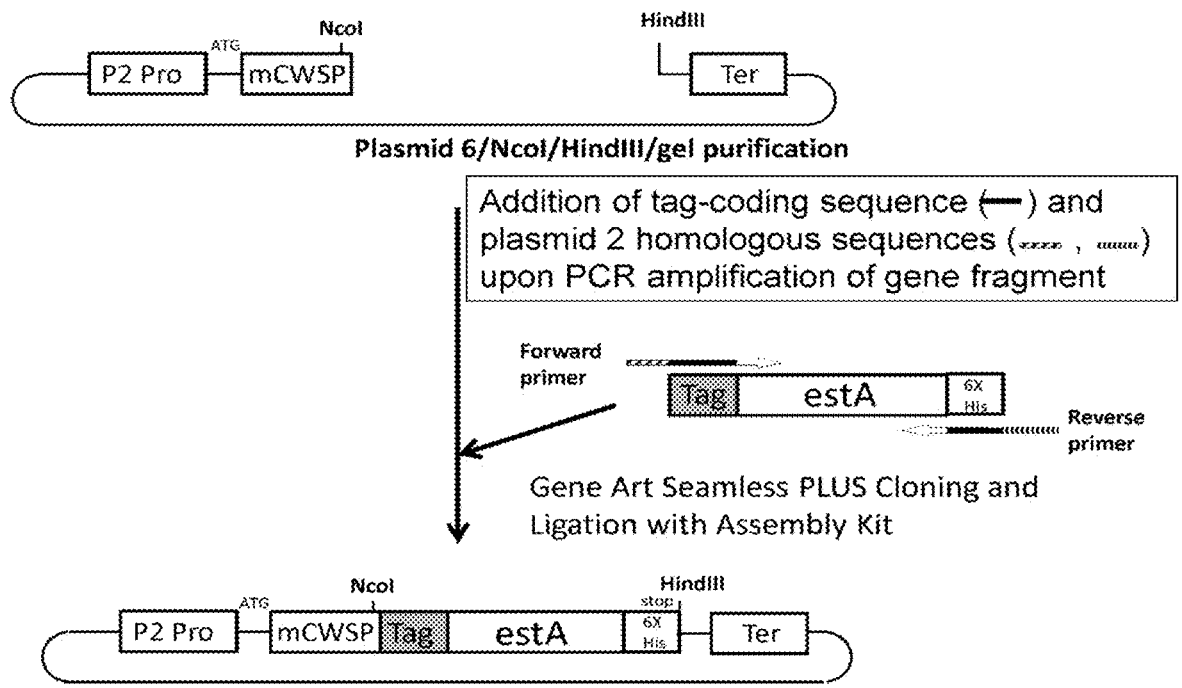
FIG. 1 is a diagram illustrating a construction procedure for a plasmid for expression, in *Brevibacillus*, of fusion proteins having various peptide tags linked to the N-terminus of esterase.

In an expression system comprising a polynucleotide introduced therein encoding a fusion protein containing: a protein of interest; and a peptide tag linked to the protein of interest and containing the following amino acid sequence; the fusion protein can be produced from the polynucleotide and accumulated in a soluble fraction. After collecting the soluble fraction, the fusion protein can be extracted.

The peptide tag used in the present invention has the following sequence.

$$X(PY)_qPZ$$

X represents an amino acid sequence composed of 0 to 5 amino acids independently selected from the group consisting of arginine (R), glycine (G), serine (S), lysine (K), threonine (T), leucine (L), asparagine (N), glutamine (Q), and methionine (M).

When X is 0 amino acid, the amino acid at the N-terminus of the peptide tag is P.

When X is 1 amino acid, the amino acid at the N-terminus of the peptide tag is selected from R, G, S, K, T, L, N, Q, and M.

When X is 1 amino acid, it is preferably Q, L, N, M, or T, more preferably Q, M, or T.

When X is 2 to 5 amino acids, the 2 to 5 X's may be either the same amino acid residues or different amino acid residues selected from R, G, S, K, T, L, N, Q, and M.

The number of X's is preferably 1 to 5, more preferably 2 to 5, still more preferably 2 or 3, especially preferably 2.

When X is 2 to 5 amino acids, the 2 amino acids in the C-terminal side, that is, the 2 amino acids immediately before (PY) q, is preferably RQ, RL, RN, RM, or RT, more preferably RQ, RM, or RT.

In (PY) q, Y represents an amino acid sequence composed of 1 to 4 amino acids independently selected from R, G, K, T, L, N, Q, and M, and q represents an integer of 1 to 10.

More specifically, the meaning of $(PY)_q$ is as follows. In PY, Y represents 1 amino acid ($PY_a$), 2 amino acids ($PY_aY_b$), 3 amino acids ($PY_aY_bY_c$), or 4 amino acids ($PY_aY_bY_cY_d$). Thus, $(PY)_q$ means that any one or more of $PY_a$, $PY_aY_b$, $PY_aY_bY_c$, and/or $PY_aY_bY_cY_d$ continue a total of q times (wherein P represents proline). PY is preferably 3 amino acids ($PY_aY_b$) or 4 amino acids ($PY_aY_bY_c$). q is an integer of 1 to 10, preferably an integer of 2 to 10, more preferably an integer of 2 to 5, still more preferably an integer of 2 or 3, especially preferably 2.

The Y's may be either the same amino acid residues or different amino acid residues selected from R, G, K, T, L, N, Q, and M. At least one of all Y's contained in the q continuous PY's (all Y's contained in the peptide tag) is preferably Q, N, L, M, or T. Two or more of the Y's are more preferably Q, N, L, M, or T. Desirably, at least one of all Y's contained in the q continuous PY's (all Y's contained in the peptide tag) is preferably Q, M, or T. Two or more of the Y's are more preferably Q, M, or T.

Each PY ($PY_1$, $PY_1Y_2$, $PY_1Y_2Y_3$, or $PY_1Y_2Y_3Y_4$) in the q continuous PY's preferably contains one Q, N, L, M, or T, more preferably contains one Q, M, or T. In Y, the amino acid(s) other than Q, N, L, M, and T is/are preferably G ('s).

For example, when Y is 2 amino acids ($PY_1Y_2$), PY is preferably PGQ, PGN, PGL, PGM, or PGT, more preferably PGQ, PGM, or PGT. When Y is 3 amino acids ($PY_1Y_2Y_3$), PY is preferably PGQG, PGNG, PGLG, PGMG, or PGTG, more preferably PGQG, PGMG, or PGTG. In one preferred mode, these continue q times in an arbitrary combination in the sequence.

Z represents an amino acid sequence composed of 0 to 10 amino acids independently selected from the group consisting of R, G, S, K, T, L, N, Q, and M.

When Z is 0 amino acid, the amino acid at the C-terminus of the peptide tag is P.

When Z is 1 amino acid, the amino acid at the C-terminus of the peptide tag is selected from R, G, S, K, T, L, N, Q, and M.

When Z is 2 to 10 amino acids, the 2 to 10 Z's may be either the same amino acid residues or different amino acid residues selected from R, G, S, K, T, L, N, Q, and M.

The number of Z's is preferably 1 to 10, more preferably 1 to 5, still more preferably 2 to 5, still more preferably 2 or 3, especially preferably 2.

When Z is 1 amino acid, it is preferably R or S, more preferably R.

When Z is 2 to 10 amino acids, the 2 amino acids in the C-terminal side, that is, the last 2 amino acids in the peptide tag, are preferably RS.

The amino acids contained in the peptide tag, that is, the amino acids contained in X, the amino acids contained in Y, and the amino acids contained in Z, preferably include three or more Q('s), N('s), L('s), M('s), and/or T('s) in total, more preferably include three or more Q('s), M('s) and/or T('s) in total. In the amino acids contained in the peptide tag, the total ratio of Q, N, L, M, and T is preferably 20 to 50%, more preferably 20 to 30%.

It should be noted that the peptide tag in which the amino acids contained therein, that is, the amino acids contained in X, the amino acids contained in Y, and the amino acids contained in Z, include three or more Q('s), N('s), L('s), M('s), and/or T('s) in total, and include at least one M, is a novel peptide tag, and that a fusion protein containing the novel peptide tag, a polynucleotide encoding it, and a recombinant vector containing the polynucleotide, per se, are included within the scope of the present invention.

The peptide tag used in the present invention has a length of preferably 6 to 50 amino acids, more preferably 6 to 40 amino acids, still more preferably 8 to 40 amino acids, still more preferably 10 to 30 amino acids, still more preferably 12 to 25 amino acid, especially preferably 12 to 20 amino acids.

Preferred examples of the peptide tag used in the present invention include peptide tags having the following sequences:

TABLE 1-1

$RXPY_1Y_2Y_3PY_4Y_5PRS$

| No. | X | $Y_1$ | $Y_2$ | $Y_3$ | $Y_4$ | $Y_5$ |
|---|---|---|---|---|---|---|
| 1-1(SEQ ID NO: 33) | Q | G | Q | G | G | Q |
| 1-2(SEQ ID NO: 34) | N | G | N | G | G | N |
| 1-3(SEQ ID NO: 35) | M | G | M | G | G | M |
| 1-4(SEQ ID NO: 36) | T | G | T | G | G | T |
| 1-5(SEQ ID NO: 37) | L | G | L | G | G | L |
| 1-6(SEQ ID NO: 38) | Q | G | Q | G | G | N |
| 1-7(SEQ ID NO: 39) | Q | G | N | G | G | Q |
| 1-8(SEQ ID NO: 40) | Q | G | N | G | G | N |
| 1-9(SEQ ID NO: 41) | Q | G | Q | G | G | M |
| 1-10(SEQ ID NO: 42) | Q | G | M | G | G | Q |
| 1-11(SEQ ID NO: 43) | Q | G | M | G | G | M |
| 1-12(SEQ ID NO: 44) | Q | G | Q | G | G | T |
| 1-13(SEQ ID NO: 45) | Q | G | T | G | G | Q |
| 1-14(SEQ ID NO: 46) | Q | G | T | G | G | T |
| 1-15(SEQ ID NO: 47) | Q | G | Q | G | G | L |
| 1-16(SEQ ID NO: 48) | Q | G | L | G | G | Q |
| 1-17(SEQ ID NO: 19) | Q | G | L | G | G | L |
| 1-18(SEQ ID NO: 50) | N | G | N | G | G | Q |
| 1-19(SEQ ID NO: 51) | N | G | Q | G | G | N |
| 1-20(SEQ ID NO: 52) | N | G | Q | G | G | Q |
| 1-21(SEQ ID NO: 53) | N | G | N | G | G | M |
| 1-22(SEQ ID NO: 54) | N | G | M | G | G | N |
| 1-23(SEQ ID NO: 55) | N | G | M | G | G | M |
| 1-24(SEQ ID NO: 56) | N | G | N | G | G | T |
| 1-25(SEQ ID NO: 57) | N | G | T | G | G | N |

TABLE 1-1-continued $RXPY_1Y_2Y_3PY_4Y_5PRS$

| No. | X | $Y_1$ | $Y_2$ | $Y_3$ | $Y_4$ | $Y_5$ |
|---|---|---|---|---|---|---|
| 1-26(SEQ ID NO: 58) | N | G | T | G | G | T |
| 1-27(SEQ ID NO: 59) | N | G | N | G | G | L |
| 1-28(SEQ ID NO: 60) | N | G | L | G | G | N |
| 1-29(SEQ ID NO: 61) | N | G | L | G | G | L |
| 1-30(SEQ ID NO: 62) | M | G | M | G | G | Q |
| 1-31(SEQ ID NO: 63) | M | G | Q | G | G | M |
| 1-32(SEQ ID NO: 64) | M | G | Q | G | G | Q |
| 1-33(SEQ ID NO: 65) | M | G | M | G | G | N |
| 1-34(SEQ ID NO: 66) | M | G | N | G | G | M |
| 1-35(SEQ ID NO: 67) | M | G | N | G | G | N |
| 1-36(SEQ ID NO: 68) | M | G | M | G | G | T |
| 1-37(SEQ ID NO: 69) | M | G | T | G | G | M |
| 1-38(SEQ ID NO: 70) | M | G | T | G | G | T |
| 1-39(SEQ ID NO: 71) | M | G | M | G | G | L |
| 1-40(SEQ ID NO: 72) | M | G | L | G | G | M |

TABLE 1-2

$RXPY_1Y_2Y_3PY_4Y_5PRS$

| No. | X | $Y_1$ | $Y_2$ | $Y_3$ | $Y_4$ | $Y_5$ |
|---|---|---|---|---|---|---|
| 1-41(SEQ ID NO: 73) | M | G | L | G | G | L |
| 1-42(SEQ ID NO: 74) | T | G | T | G | G | Q |
| 1-43(SEQ ID NO: 75) | T | G | Q | G | G | T |
| 1-44(SEQ ID NO: 76) | T | G | Q | G | G | Q |
| 1-45(SEQ ID NO: 77) | T | G | T | G | G | N |
| 1-46(SEQ ID NO: 78) | T | G | N | G | G | T |
| 1-47(SEQ ID NO: 79) | T | G | N | G | G | N |
| 1-48(SEQ ID NO: 80) | T | G | T | G | G | M |
| 1-49(SEQ ID NO: 81) | T | G | M | G | G | T |
| 1-50(SEQ ID NO: 82) | T | G | M | G | G | M |
| 1-51(SEQ ID NO: 83) | T | G | T | G | G | L |
| 1-52(SEQ ID NO: 84) | T | G | L | G | G | T |
| 1-53(SEQ ID NO: 85) | T | G | L | G | G | L |
| 1-54(SEQ ID NO: 86) | L | G | L | G | G | Q |
| 1-55(SEQ ID NO: 87) | L | G | Q | G | G | L |
| 1-56(SEQ ID NO: 88) | L | G | Q | G | G | Q |
| 1-57(SEQ ID NO: 89) | L | G | L | G | G | N |
| 1-58(SEQ ID NO: 90) | L | G | N | G | G | L |
| 1-59(SEQ ID NO: 91) | L | G | N | G | G | N |
| 1-60(SEQ ID NO: 92) | L | G | L | G | G | M |
| 1-61(SEQ ID NO: 93) | L | G | M | G | G | L |
| 1-62(SEQ ID NO: 94) | L | G | M | G | G | M |
| 1-63(SEQ ID NO: 95) | L | G | L | G | G | T |
| 1-64(SEQ ID NO: 96) | L | G | T | G | G | L |
| 1-65(SEQ ID NO: 97) | L | G | T | G | G | T |
| 1-66(SEQ ID NO: 98) | Q | Q | Q | Q | Q | Q |
| 1-67(SEQ ID NO: 99) | N | N | N | N | N | N |
| 1-68(SEQ ID NO: 100) | M | M | M | M | M | M |
| 1-69(SEQ ID NO: 101) | T | T | T | T | T | T |
| 1-70(SEQ ID NO: 102) | L | L | L | L | L | L |

TABLE 1-3

$RXPY_1Y_2Y_3PY_4Y_5GRS$

| No. | X | $Y_1$ | $Y_2$ | $Y_3$ | $Y_4$ | $Y_5$ |
|---|---|---|---|---|---|---|
| 2-1(SEQ ID NO: 103) | Q | G | Q | G | G | Q |
| 2-2(SEQ ID NO: 104) | N | G | N | G | G | N |
| 2-3(SEQ ID NO: 105) | M | G | M | G | G | M |
| 2-4(SEQ ID NO: 106) | T | G | T | G | G | T |
| 2-5(SEQ ID NO: 107) | L | G | L | G | G | L |
| 2-6(SEQ ID NO: 108) | Q | G | Q | G | G | N |
| 2-7(SEQ ID NO: 109) | Q | G | N | G | G | Q |
| 2-8(SEQ ID NO: 110) | Q | G | N | G | G | N |
| 2-9(SEQ ID NO: 111) | Q | G | Q | G | G | M |
| 2-10(SEQ ID NO: 112) | Q | G | M | G | G | Q |
| 2-11(SEQ ID NO: 113) | Q | G | M | G | G | M |
| 2-12(SEQ ID NO: 114) | Q | G | Q | G | G | T |

TABLE 1-3-continued $RXPY_1Y_2Y_3PY_4Y_5GRS$

| No. | X | $Y_1$ | $Y_2$ | $Y_3$ | $Y_4$ | $Y_5$ |
|---|---|---|---|---|---|---|
| 2-13(SEQ ID NO: 115) | Q | G | T | G | G | Q |
| 2-14(SEQ ID NO: 116) | Q | G | T | G | G | T |
| 2-15(SEQ ID NO: 117) | Q | G | Q | G | G | L |
| 2-16(SEQ ID NO: 118) | Q | G | L | G | G | Q |
| 2-17(SEQ ID NO: 119) | Q | G | L | G | G | L |
| 2-18(SEQ ID NO: 120) | N | G | N | G | G | Q |
| 2-19(SEQ ID NO: 121) | N | G | Q | G | G | N |
| 2-20(SEQ ID NO: 122) | N | G | Q | G | G | Q |
| 2-21(SEQ ID NO: 123) | N | G | N | G | G | M |
| 2-22(SEQ ID NO: 124) | N | G | M | G | G | N |
| 2-23(SEQ ID NO: 125) | N | G | M | G | G | M |
| 2-24(SEQ ID NO: 126) | N | G | N | G | G | T |
| 2-25(SEQ ID NO: 127) | N | G | T | G | G | N |
| 2-26(SEQ ID NO: 128) | N | G | T | G | G | T |
| 2-27(SEQ ID NO: 129) | N | G | N | G | G | L |
| 2-28(SEQ ID NO: 130) | N | G | L | G | G | N |
| 2-29(SEQ ID NO: 131) | N | G | L | G | G | L |
| 2-30(SEQ ID NO: 132) | M | G | M | G | G | Q |
| 2-31(SEQ ID NO: 133) | M | G | Q | G | G | M |
| 2-32(SEQ ID NO: 134) | M | G | Q | G | G | Q |
| 2-33(SEQ ID NO: 135) | M | G | M | G | G | N |
| 2-34(SEQ ID NO: 136) | M | G | N | G | G | M |
| 2-35(SEQ ID NO: 137) | M | G | N | G | G | N |
| 2-36(SEQ ID NO: 138) | M | G | M | G | G | T |
| 2-37(SEQ ID NO: 139) | M | G | T | G | G | M |
| 2-38(SEQ ID NO: 140) | M | G | T | G | G | T |
| 2-39(SEQ ID NO: 141) | M | G | M | G | G | L |
| 2-40(SEQ ID NO: 142) | M | G | L | G | G | M |

TABLE 1-4

$RXPY_1Y_2Y_3PY_4Y_5GRS$

| No. | X | $Y_1$ | $Y_2$ | $Y_3$ | $Y_4$ | $Y_5$ |
|---|---|---|---|---|---|---|
| 2-41(SEQ ID NO: 143) | M | G | L | G | G | L |
| 2-42(SEQ ID NO: 144) | T | G | T | G | G | Q |
| 2-43(SEQ ID NO: 145) | T | G | Q | G | G | T |
| 2-44(SEQ ID NO: 146) | T | G | Q | G | G | Q |
| 2-45(SEQ ID NO: 147) | T | G | T | G | G | N |
| 2-46(SEQ ID NO: 148) | T | G | N | G | G | T |
| 2-47(SEQ ID NO: 149) | T | G | N | G | G | N |
| 2-48(SEQ ID NO: 150) | T | G | T | G | G | M |
| 2-49(SEQ ID NO: 151) | T | G | M | G | G | T |
| 2-50(SEQ ID NO: 152) | T | G | M | G | G | M |
| 2-51(SEQ ID NO: 153) | T | G | T | G | G | L |
| 2-52(SEQ ID NO: 154) | T | G | L | G | G | T |
| 2-53(SEQ ID NO: 155) | T | G | L | G | G | L |
| 2-54(SEQ ID NO: 156) | L | G | L | G | G | Q |
| 2-55(SEQ ID NO: 157) | L | G | Q | G | G | L |
| 2-56(SEQ ID NO: 158) | L | G | Q | G | G | Q |
| 2-57(SEQ ID NO: 159) | L | G | L | G | G | N |
| 2-58(SEQ ID NO: 160) | L | G | N | G | G | L |
| 2-59(SEQ ID NO: 161) | L | G | N | G | G | N |
| 2-60(SEQ ID NO: 162) | L | G | L | G | G | M |
| 2-61(SEQ ID NO: 163) | L | G | M | G | G | L |
| 2-62(SEQ ID NO: 164) | L | G | M | G | G | M |
| 2-63(SEQ ID NO: 165) | L | G | L | G | G | T |
| 2-64(SEQ ID NO: 166) | L | G | T | G | G | L |
| 2-65(SEQ ID NO: 167) | L | G | T | G | G | T |
| 2-66(SEQ ID NO: 168) | Q | Q | Q | Q | Q | Q |
| 2-67(SEQ ID NO: 169) | N | N | N | N | N | N |
| 2-68(SEQ ID NO: 170) | M | M | M | M | M | M |
| 2-69(SEQ ID NO: 171) | T | T | T | T | T | T |
| 2-70(SEQ ID NO: 172) | L | L | L | L | L | L |

TABLE 1-5

RXPY₁PY₂PY₃PY₄PY₅RS

| No. | X | Y₁ | Y₂ | Y₃ | Y₄ | Y₅ |
|---|---|---|---|---|---|---|
| 3-1(SEQ ID NO: 173) | Q | G | Q | G | Q | G |
| 3-2(SEQ ID NO: 174) | N | G | N | G | N | G |
| 3-3(SEQ ID NO: 175) | M | G | M | G | M | G |
| 3-4(SEQ ID NO: 176) | T | G | T | G | T | G |
| 3-5(SEQ ID NO: 177) | L | G | L | G | L | G |
| 3-6(SEQ ID NO: 178) | Q | G | Q | G | N | G |
| 3-7(SEQ ID NO: 179) | Q | G | N | G | Q | G |
| 3-8(SEQ ID NO: 180) | Q | G | N | G | N | G |
| 3-9(SEQ ID NO: 181) | Q | G | Q | G | M | G |
| 3-10(SEQ ID NO: 182) | Q | G | M | G | Q | G |
| 3-11(SEQ ID NO: 183) | Q | G | M | G | M | G |
| 3-12(SEQ ID NO: 184) | Q | G | Q | G | T | G |
| 3-13(SEQ ID NO: 185) | Q | G | T | G | Q | G |
| 3-14(SEQ ID NO: 186) | Q | G | T | G | T | G |
| 3-15(SEQ ID NO: 187) | Q | G | Q | G | L | G |
| 3-16(SEQ ID NO: 188) | Q | G | L | G | Q | G |
| 3-17(SEQ ID NO: 189) | Q | G | L | G | L | G |
| 3-18(SEQ ID NO: 190) | N | G | N | G | Q | G |
| 3-19(SEQ ID NO: 191) | N | G | Q | G | N | G |
| 3-20(SEQ ID NO: 192) | N | G | Q | G | Q | G |
| 3-21(SEQ ID NO: 193) | N | G | N | G | M | G |
| 3-22(SEQ ID NO: 194) | N | G | M | G | N | G |
| 3-23(SEQ ID NO: 195) | N | G | M | G | M | G |
| 3-24(SEQ ID NO: 196) | N | G | N | G | T | G |
| 3-25(SEQ ID NO: 197) | N | G | T | G | N | G |
| 3-26(SEQ ID NO: 198) | N | G | T | G | T | G |
| 3-27(SEQ ID NO: 199) | N | G | N | G | L | G |
| 3-28(SEQ ID NO: 200) | N | G | L | G | N | G |
| 3-29(SEQ ID NO: 201) | N | G | L | G | L | G |
| 3-30(SEQ ID NO: 202) | M | G | M | G | Q | G |
| 3-31(SEQ ID NO: 203) | M | G | Q | G | M | G |
| 3-32(SEQ ID NO: 204) | M | G | Q | G | Q | G |
| 3-33(SEQ ID NO: 205) | M | G | M | G | N | G |
| 3-34(SEQ ID NO: 206) | M | G | N | G | M | G |
| 3-35(SEQ ID NO: 207) | M | G | N | G | N | G |
| 3-36(SEQ ID NO: 208) | M | G | M | G | T | G |
| 3-37(SEQ ID NO: 209) | M | G | T | G | M | G |
| 3-38(SEQ ID NO: 210) | M | G | T | G | T | G |
| 3-39(SEQ ID NO: 211) | M | G | M | G | L | G |
| 3-40(SEQ ID NO: 212) | M | G | L | G | M | G |

TABLE 1-6

RXPY₁PY₂PY₃PY₄PY₅RS

| No. | X | Y₁ | Y₂ | Y₃ | Y₄ | Y₅ |
|---|---|---|---|---|---|---|
| 3-41(SEQ ID NO: 213) | M | G | L | G | L | G |
| 3-42(SEQ ID NO: 214) | T | G | T | G | Q | G |
| 3-43(SEQ ID NO: 215) | T | G | Q | G | T | G |
| 3-44(SEQ ID NO: 216) | T | G | Q | G | Q | G |
| 3-45(SEQ ID NO: 217) | T | G | T | G | N | G |
| 3-46(SEQ ID NO: 218) | T | G | N | G | T | G |
| 3-47(SEQ ID NO: 219) | T | G | N | G | N | G |
| 3-48(SEQ ID NO: 220) | T | G | T | G | M | G |
| 3-49(SEQ ID NO: 221) | T | G | M | G | T | G |
| 3-50(SEQ ID NO: 222) | T | G | M | G | M | G |
| 3-51(SEQ ID NO: 223) | T | G | T | G | L | G |
| 3-52(SEQ ID NO: 224) | T | G | L | G | T | G |
| 3-53(SEQ ID NO: 225) | T | G | L | G | L | G |
| 3-54(SEQ ID NO: 226) | L | G | L | G | Q | G |
| 3-55(SEQ ID NO: 227) | L | G | Q | G | L | G |
| 3-56(SEQ ID NO: 228) | L | G | Q | G | Q | G |
| 3-57(SEQ ID NO: 229) | L | G | L | G | N | G |
| 3-58(SEQ ID NO: 230) | L | G | N | G | L | G |
| 3-59(SEQ ID NO: 231) | L | G | N | G | N | G |
| 3-60(SEQ ID NO: 232) | L | G | L | G | M | G |
| 3-61(SEQ ID NO: 233) | L | G | M | G | L | G |
| 3-62(SEQ ID NO: 234) | L | G | M | G | M | G |
| 3-63(SEQ ID NO: 235) | L | G | L | G | T | G |
| 3-64(SEQ ID NO: 236) | L | G | T | G | L | G |
| 3-65(SEQ ID NO: 237) | L | G | T | G | T | G |
| 3-66(SEQ ID NO: 238) | Q | Q | Q | Q | Q | Q |

TABLE 1-6-continued

RXPY₁PY₂PY₃PY₄PY₅RS

| No. | X | Y₁ | Y₂ | Y₃ | Y₄ | Y₅ |
|---|---|---|---|---|---|---|
| 3-67(SEQ ID NO: 239) | N | N | N | N | N | N |
| 3-68(SEQ ID NO: 240) | M | M | M | M. | M | M |
| 3-69(SEQ ID NO: 241) | T | T | T | T | T | T |
| 3-70(SEQ ID NO: 242) | L | L | L | L | L | L |

In the present invention, the fusion protein is a protein in which the peptide tag is linked to a protein of interest. The peptide tag may be linked to the N-terminus of the protein of interest; the peptide tag may be linked to the C-terminus of the protein of interest; or the peptide tag may be linked to each of the N-terminus and C-terminus of the protein of interest. The peptide tag(s) may be directly linked to the N-terminus and/or C-terminus of the protein of interest, or may be linked thereto through a sequence(s) of one to several amino acids (for example, 1 to 5 amino acids). The sequence of one to several amino acids may be an arbitrary sequence as long as the sequence does not adversely affect the function and the expression level of the protein of interest. In cases where the sequence is a protease recognition sequence, the peptide tag may be cleaved off from the protein of interest after the expression and purification. Examples of the protease recognition sequence include a factor Xa recognition sequence. The fusion protein may also include another tag sequence required for detection or purification, such as a His tag, HN tag, or FLAG tag.

The type of the protein of interest contained in the fusion protein is not limited. The protein of interest is preferably a protein to be used for medical application, diagnosis, or material production. Examples of the protein of interest include growth factors, hormones, cytokines, blood proteins, enzymes, antigens, antibodies, transcription factors, receptors, fluorescent proteins, and partial peptides thereof.

Examples of the enzymes include lipase, protease, steroid-synthesizing enzymes, kinase, phosphatase, xylanase, esterase, methylase, demethylase, oxidase, reductase, cellulase, aromatase, collagenase, transglutaminase, glycosidase, and chitinase.

Examples of the growth factors include epidermal growth factor (EGF), insulin-like growth factor (IGF), transforming growth factor (TGF), nerve growth factor (NGF), brain-derived neurotrophic factor (BDNF), vascular endothelial growth factor (VEGF), granulocyte colony-stimulating factor (G-CSF), granulocyte-macrophage colony-stimulating factor (GM-CSF), platelet-derived growth factor (PDGF), erythropoietin (EPO), thrombopoietin (TPO), fibroblast growth factor (FGF), and hepatocyte growth factor (HGF).

Examples of the hormones include insulin, glucagon, somatostatin, growth hormone, parathyroid hormone, prolactin, leptin, and calcitonin.

Examples of the cytokines include interleukins, interferons (IFNα, IFNβ, IFNγ), and tumor necrosis factor (TNF).

Examples of the blood proteins include thrombin, serum albumin, factor VII, factor VIII, factor IX, factor X, and tissue plasminogen activator.

Examples of the antibodies include complete antibodies, Fab, F(ab'), F(ab')₂, Fc, Fc fusion proteins, heavy chain (H-chain), light chain (L-chain), single-chain Fv (scFv), sc(Fv)₂, disulfide-linked Fv (sdFv), and diabodies.

For use as vaccines, the antigen proteins are not limited as long as the immune response can be induced therewith. The antigen proteins may be appropriately selected depending on the expected target of the immune response. Examples of the antigen proteins include proteins derived from pathogenic bacteria and proteins derived from pathogenic viruses.

To the fusion protein, a secretion signal peptide that functions in a host cell may be added for secretory production. Examples of the secretion signal peptide include: invertase secretion signal, P3 secretion signal, and α-factor secretion signal in cases where yeast is used as the host; PelB secretion signal in cases where *E. coli* is used as the host; and P2 secretion signal and P22 secretion signal in cases where *Brevibacillus* is used as the host. When a plant is used as the host, examples of the secretion signal include those derived from tobacco (*Nicotiana tabacum*), *Arabidopsis thaliana*, strawberry (*Fragaria* x *ananassa*), lettuce (*Lactuca sativa*), or the like.

For allowing expression of the fusion protein in a particular cellular compartment, a transport signal peptide such as an endoplasmic reticulum retention signal peptide or a vacuole transport signal peptide may be added thereto.

By introducing a polynucleotide encoding the fusion protein into an expression system, the fusion protein can be produced by genetic engineering.

In the present invention, the polynucleotide means a substance having a base sequence carrying genetic information encoding the fusion protein. Examples of the polynucleotide include DNA and RNA. More specifically, the polynucleotide encoding the fusion protein contains a polynucleotide encoding the protein of interest and a polynucleotide encoding the peptide tag, wherein the polynucleotide encoding the protein of interest is linked to the polynucleotide encoding the peptide tag in the same reading frame.

The polynucleotide encoding the protein of interest may be obtained by, for example, a common genetic engineering method based on a known base sequence.

Preferably, in the polynucleotide encoding the fusion protein, a codon(s) corresponding to an amino acid(s) constituting the fusion protein is/are modified as appropriate such that the translation level of the fusion protein increases depending on the host cell in which the protein is to be produced. For the method of the codon modification, one may refer to, for example, the method of Kang et al. (Protein Expr Purif. 2004 November; 38 (1): 129-35). Examples of the method also include methods in which codons frequently used in the host cell are selected, methods in which codons with high GC contents are selected, and methods in which codons frequently used in housekeeping genes of the host cell are selected.

For improving expression in the host cell, the polynucleotide encoding the fusion protein may contain an enhancer sequence or the like that functions in the host cell.

The polynucleotide encoding the fusion protein may be prepared by a common genetic engineering method. For example, a DNA encoding the peptide tag, a DNA encoding the protein of interest, and the like may be linked to each other using PCR, DNA ligase, and/or the like, to construct the polynucleotide.

The polynucleotide encoding the fusion protein may be introduced as it is into the expression system. The polynucleotide is, however, preferably introduced into the expression system as a recombinant vector containing the polynucleotide.

The recombinant vector may be a vector in which the polynucleotide encoding the fusion protein is inserted such that the expression is possible in the host cell to which the vector is to be introduced. The vector is not limited as long as it can replicate in the host cell. Examples of the vector include plasmid DNAs and viral DNAs. The vector preferably contains a selection marker such as a drug resistance gene. Specific examples of the plasmid vectors include pTrcHis2 vector, pUC119, pBR322, pBluescript II KS+, pYES2, pAUR123, pQE-Tri, pET, pGEM-3Z, pGEX, pMAL, pRI909, pRI910, pBI221, pBI121, pNCMO2, pBI101, pIG121Hm, pTrc99A, pKK223, pA1-11, pXT1, pRc/CMV, pRc/RSV, pcDNA I/Neo, p3×FLAG-CMV-14, pCAT3, pcDNA3.1, and pCMV.

The promoter used in the vector may be appropriately selected depending on the host cell to which the vector is to be introduced. In cases of expression in yeast, examples of the promoter that may be used include the GAL1 promoter, PGK1 promoter, TEF1 promoter, ADH1 promoter, TPI1 promoter, and PYK1 promoter. In cases of expression in mammalian cells, examples of the promoter that may be used include the CMV promoter, SV40 promoter, and EF1α promoter. In cases of expression in a plant, examples of the promoter that may be used include the cauliflower mosaic virus 35S promoter, rice actin promoter, maize ubiquitin promoter, and lettuce ubiquitin promoter. In cases of expression in *E. coli*, examples of the promoter include the T7 promoter. In cases of expression in *Brevibacillus*, examples of the promoter include the P2 promoter and the P22 promoter. The promoter may be an inducible promoter. Examples of the inducible promoter that may be used include lac, tac, and trc, which are inducible with IPTG; trp, which is inducible with IAA; ara, which is inducible with L-arabinose; Pzt-1, which is inducible with tetracycline; the Pz promoter, which is inducible by heat (42° C.); and the promoter of the cspA gene, which is a cold shock gene.

When necessary, a terminator sequence may also be included depending on the host cell.

The recombinant vector may be prepared by, for example, cleaving a DNA encoding the fusion protein with an appropriate restriction enzyme, or adding a restriction site thereto by PCR, and then inserting the resulting DNA into a restriction site or a multicloning site in a vector.

In the present invention, the polynucleotide encoding the fusion protein, or the recombinant vector containing it, may be introduced into an expression system, and may then be allowed to express the fusion protein in the expression system, to enable efficient accumulation of the fusion protein in a soluble fraction.

The expression system herein means a system comprising translation factors required for protein expression, such as ribosomes, tRNAs, and amino acids, which system is capable of producing a fusion protein from the polynucleotide encoding the fusion protein, or from a recombinant vector containing it. Examples of the expression system include: prokaryotic cells, such as bacterial cells, including *E. coli*, *Bacillus* (bacteria belonging to the genus *Bacillus*), bacteria belonging to the genus *Brevibacillus*, actinomycetes, corynebacteria, and cyanobacteria; and eukaryotic cells, such as yeast cells including baker's yeast, *Pichia* yeast, and fission yeast, aspergilli, insect cells, mammalian cells, and plant cells. Examples of the expression system also include: cell-free protein expression systems derived from prokaryotic cells such as *E. coli*; and cell-free protein expression systems derived from eukaryotic cells such as reticulocytes, wheat germ, or insect cell extracts.

The expression system is preferably transformed cells obtained by transformation of an expression system with the polynucleotide encoding the fusion protein, or with a recombinant vector containing it. The transformed cells may be prepared by introducing the polynucleotide or recombinant vector encoding the fusion protein into host cells, using a common genetic engineering method. Examples of the method that may be used include the electroporation method (Tada, et al., 1990, Theor. Appl. Genet, 80:475), the protoplast method (Gene, 39, 281-286 (1985)), the polyethylene glycol method (Lazzeri, et al., 1991, Theor. Appl. Genet. 81:437), introduction methods utilizing *Agrobacterium* (Hood, et al., 1993, Transgenic, Res. 2:218, Hiei, et al., 1994 Plant J. 6:271), the particle gun method (Sanford, et al., 1987, J. Part. Sci. tech. 5:27), and the polycation method (Ohtsuki, et al., FEBS Lett. 1998 May 29; 428 (3): 235-40). The gene expression may be transient expression, or may be stable expression based on incorporation into the chromosome. The transformant may be selected utilizing a selection marker such as a drug resistance gene.

In the expression systems such as the transformed cells and the cell-free protein expression systems, the fusion protein is accumulated in a soluble fraction. Conditions for the protein expression, such as the medium, temperature, and time, may be appropriately selected in accordance with the type of the expression system.

The soluble fraction means a fraction containing the medium outside the cells, the intracellular liquid fraction which contains neither nuclei nor organelles, and the like. The soluble fraction thus means a fraction from which the fusion protein can be collected as a solution.

The fusion protein is preferably produced as a nondenatured protein. The nondenatured protein herein means a protein which maintains its higher-order structure, and which has not undergone changes such as activity loss or insolubilization, or has undergone such changes only to a small extent.

By collecting the soluble fraction, a solution containing the nondenatured protein can be obtained.

The solution containing the nondenatured protein herein means a state where the nondenatured protein is solubilized in water in the cells and outside the cells. It is a state where, in the cells, the expressed protein is located, without aggregation, in the cytosol or in its proper positions in the cells such that the protein can easily exert its original function or activity, and where, outside the cells, the protein of interest is solubilized, without aggregation, in a solvent composed mainly of water, such that the solubilized protein has its original function or activity.

The fusion protein accumulated in the soluble fraction may be used as it is for enzymatic reaction or the like. Alternatively, the fusion protein may be separated and purified according to a method well known to those skilled in the art. For example, the separation and purification may be carried out by an appropriate known method such as salting-out, ethanol precipitation, ultrafiltration, gel filtration chromatography, ion-exchange column chromatography, affinity chromatography, high/medium-pressure liquid chromatography, reversed-phase chromatography, or hydrophobic chromatography, or by combination of any of these.

EXAMPLES

Examples of the present invention are described below, but the present invention is not limited to the Examples.
(1) Construction of Gene Expression Plasmid Encoding Peptide-Tagged Esterase for *Brevibacillus*, and Transformation Therewith An artificial synthetic DNA (SEQ ID NO:26) encoding esterase derived from *Bacillus subtilis* (EstA, SEQ ID NO:25) was inserted into the EcoRV recognition site of the pUC19-modified plasmid pUCFa (Fasmac), thereby plasmid 1 was obtained.

As a plasmid for expression in *Brevibacillus*, pNCMO2 (Takara Bio Inc.) was used (plasmid 2).

Figure 2:
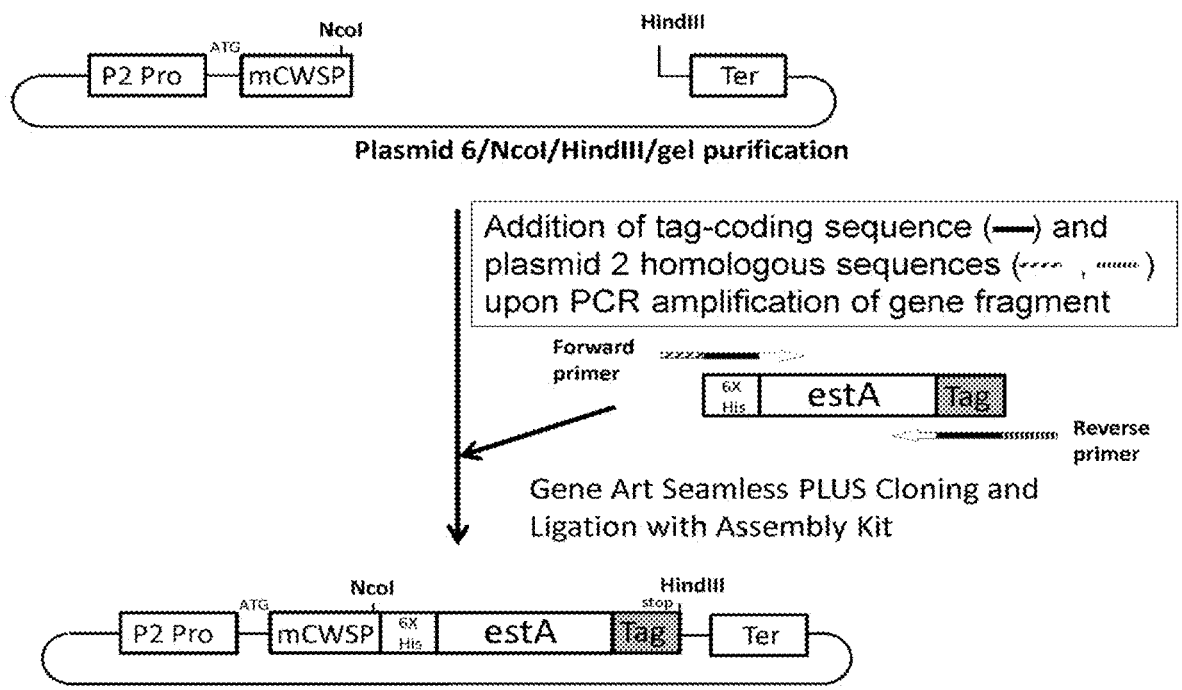
FIG. 2 is a diagram illustrating a construction procedure for a plasmid for expression, in *Brevibacillus*, of fusion proteins having various peptide tags linked to the C-terminus of esterase.

By the following procedure, plasmids for expressing, in *Brevibacillus*, fusion proteins in which various peptide tags are added to the N-terminus of esterase, and in which a 6×His tag for detection and purification is added to the C-terminus, and fusion proteins in which a 6×His tag for detection and purification is added to the N-terminus of esterase, and in which various peptide tags are added to the C-terminus, were constructed (FIGS. 1 and 2).

TABLE 2

Amino acid sequence of each peptide tag

| No. | Tag | Position of addition | Amino acid sequence |
|---|---|---|---|
| Comparative Example 1 | Tag(-)-N | — | — |
| Comparative Example 2 | PG12-N | N terminus | RSPGSGPGSPRS (SEQ ID NO: 1) |
| Comparative Example 3 | PX12-20-N | N terminus | RKPGKGPGKPRS (SEQ ID NO: 4) |
| Example 1 1-1 | PX12-32-N | N terminus | RQPGQGPGQPRS (SEQ ID NO: 7) |
| Example 2 1-2 | PX12-33-N | N terminus | RNPGNGPGNPRS (SEQ ID NO: 10) |
| Example 3 1-3 | PX12-34-N | N terminus | RMPGMGPGMPRS (SEQ ID NO: 12) |
| Example 4 1-4 | PX12-35-N | N terminus | RTPGTGPGTPRS (SEQ ID NO: 15) |
| Example 5 1-5 | PX12-36-N | N terminus | RLPGLGPGLPRS (SEQ ID NO: 17) |
| Example 6 1-66 | PX12-90-N | N terminus | RQPQQQPQQPRS (SEQ ID NO: 23) |
| Example 7 2-1 | PX12-89-N | N-terminus | RQPGQGPGQGRS (SEQ ID NO: 21) |
| Example 8 3-3 | PX12-83-N | N terminus | RMPGMPGMPGRS (SEQ ID NO: 19) |
| Comparative Example 4 | Tag(-)-C | — | — |
| Comparative Example 5 | PG12-C | C terminus | RSPGSGPGSPRS (SEQ ID NO: 1) |
| Comparative Example 6 | PX12-20-C | C terminus | RKPGKGPGKPRS (SEQ ID NO: 4) |
| Example 9 1-1 | PX12-32-C | C terminus | RQPGQGPGQPRS (SEQ ID NO: 7) |
| Exmample 10 1-3 | PX12-34-C | C terminus | RMPGMGPGMPRS (SEQ ID NO: 10) |

First, for the addition of the various peptide tags to the N- or C-terminus of esterase, PCR was carried out using the combinations of a template plasmid, a forward primer, and a reverse primer shown in Table 3.

TABLE 3

Template plasmid and primers used for PCR amplification of BsestA gene added with peptide tag-coding sequence

| PCR amplified fragment | Added peptide tag sequence | | Template | | |
|---|---|---|---|---|---|
| | N terminus | C terminus | Plasmid | Forward primer | Reverse primer |
| Tag-(—)-N | — | — | Plasmid1 | mCWSP-AD-BsestAF (SEQ ID NO: 29) | BsestAR-6xHis-stopXt (SEQ ID NO: 32) |
| Tag-(—)-C | — | — | Plasmid1 | mCWSP-AD-6xHis-BsestAF (SEQ ID NO: 31) | BsestAR-stopXt (SEQ ID NO: 30) |
| BsestA-PG12-N | SEQ ID NO: 1 | — | Plasmid1 | mCWSP-AD-PG12-BsestAF (SEQ ID NO: 2) | BsestAR-6xHis-stopXt (SEQ ID NO: 32) |
| BsestA-PG12-C | — | SEQ ID NO: 1 | Plasmid1 | mCWSP-AD-6xHis-BsestAF (SEQ ID NO: 31) | BsestAR-PG12-stopXt (SEQ ID NO: 3) |
| BsestA-PX12-20-N | SEQ ID NO: 4 | — | Plasmid1 | mCWSP-AD-PX12-20-BsestAF (SEQ ID NO: 5) | BsestAR-6xHis-stopXt (SEQ ID NO: 32) |
| BsestA-PX12-20-C | — | SEQ ID NO: 4 | Plasmid1 | mCWSP-AD-6xHis-BsestAF (SEQ ID NO: 31) | BsestAR-PX12-stopXt (SEQ ID NO: 6) |
| BsestA-PX12-32-N | SEQ ID NO: 7 | — | Plasmid1 | mCWSP-AD-PX12-32-BsestAF (SEQ ID NO: 8) | BsestAR-6xHis-stopXt (SEQ ID NO: 32) |
| BsestA-PX12-32-C | — | SEQ ID NO: 7 | Plasmid1 | mCWSP-AD-6xHis-BsestAF (SEQ ID NO: 31) | BsestAR-PX12-stopXt (SEQ ID NO: 9) |
| BsestA-PX12-33-N | SEQ ID NO: 10 | — | Plasmid1 | mCWSP-AD-PX12-33-BsestAF (SEQ ID NO: 11) | BsestAR-6xHis-stopXt (SEQ ID NO: 32) |
| BsestA-PX12-34-N | SEQ ID NO: 12 | — | Plasmid1 | mCWSP-AD-PX12-34-BsestAF (SEQ ID NO: 13) | BsestAR-6xHis-stopXt (SEQ ID NO: 32) |
| BsestA-PX12-34-C | — | SEQ ID NO: 12 | Plasmid1 | mCWSP-AD-6xHis-BsestAF (SEQ ID NO: 31) | BsestAR-PX12-stopXt (SEQ ID NO: 14) |
| BsestA-PX12-35-N | SEQ ID NO: 15 | — | Plasmid1 | mCWSP-AD-PX12-35-BsestAF (SEQ ID NO: 16) | BsestAR-6xHis-stopXt (SEQ ID NO: 32) |
| BsestA-PX12-36-N | SEQ ID NO: 17 | — | Plasmid1 | mCWSP-AD-PX12-36-BsestAF (SEQ ID NO: 18) | BsestAR-6xHis-stopXt (SEQ ID NO: 32) |
| BsestA-PX12-83-N | SEQ ID NO: 19 | — | Plasmid1 | mCWSP-AD-PX12-83-BsestAF (SEQ ID NO: 20) | BsestAR-6xHis-stopXt (SEQ ID NO: 32) |
| BsestA-PX12-89-N | SEQ ID NO: 21 | — | Plasmid1 | mCWSP-AD-PX12-89-BsestAF (SEQ ID NO: 22) | BsestAR-6xHis-stopXt (SEQ ID NO: 32) |
| BsestA-PX12-90-N | SEQ ID NO: 23 | — | Plasmid1 | mCWSP-AD-PX12-90-BsestAF (SEQ ID NO: 24) | BsestAR-6xHis-stopXt (SEQ ID NO: 32) |

To the 5'-end of each primer, a sequence homologous to plasmid 2 was added. In designing of the forward primer, the 2 amino acid residues AD were added such that they follow a signal peptide. For the PCR, KOD-PLUS-Ver. 2 (Toyobo Co., Ltd.) was used. A reaction liquid in an amount of 50 µl was prepared such that it contained 2 pg/µl template plasmid, 0.3 µM forward primer, 0.3 µM reverse primer, 0.2 mM dNTPs, 1× Buffer for KOD-Plus-Ver. 2, 1.5 mM MgSO$_4$, and 0.02 U/µl KOD-PLUS-Ver. 2. The reaction liquid was heated at 94° C. for 5 minutes, and this was followed by 30 cycles of treatment each composed of heating at 98° C. for 10 seconds, at 60° C. for 30 seconds, and then at 68° C. for 40 seconds. Finally, the reaction liquid was heated at 68° C. for 5 minutes.

The resulting amplification fragment was purified with a QIAquick PCR Purification Kit (Qiagen).

Plasmid 2 was digested with NcoI and HindIII, and then separated by electrophoresis using 0.8% SeaKem GTG Agarose, followed by extraction from the gel using a QIAquick Gel Extraction Kit (Qiagen).

About 50 ng of the extracted plasmid 2 was mixed with 2 µl of the purified PCR product, and the liquid volume was adjusted to 5 µl. The resulting mixture was mixed with 5 µl of 2× Enzyme Mix included in a Gene Art Seamless PLUS Cloning and Assembly Kit (Thermo Fisher Scientific), and then left to stand at room temperature for 30 minutes, followed by being left to stand on ice for 5 minutes.

With competent cells DH5-α, 5 µl of the reaction liquid was mixed, and the resulting mixture was left to stand on ice for 30 minutes. The mixture was then warmed at 42° C. for 45 seconds, and left to stand on ice for 2 minutes, followed by addition of 250 µl of SOC thereto and shaking at 37° C. at 200 rpm for 1 hour. Subsequently, 50 µl of the shaken product was applied to 2×YT agar medium supplemented with 100 mg/l ampicillin, and static culture was carried out at 37° C. overnight, to obtain transformed colonies. A colony was transferred to 2×YT liquid medium supplemented with 100 mg/l ampicillin, and shake culture was carried out at 37° C. at 200 rpm overnight, followed by extraction of the plasmid for gene expression. After confirmation of the base sequence, the plasmid was used for transformation of Brevibacillus.

Competent cells of the Brevibacillus choshinensis SP3 strain were left to stand on a heat block at 37° C. for 30 seconds to allow rapid thawing, and then centrifuged (12,000 rpm, room temperature, 1 minute). After removing the supernatant, the whole amount of a mixture of 1 µl of the above plasmid solution for gene expression and 50 µl of Solution A was added to the cells, and the pellet of the competent cells was completely suspended by vortexing, followed by leaving the resulting suspension to stand for 5 minutes. After addition of 150 µl of Solution B, the suspension was mixed by vortexing for 10 seconds, and then centrifugation was carried out (5000 rpm, room temperature, 5 minutes), followed by removing the supernatant. After carrying out centrifugation (5000 rpm, room temperature, 30 seconds) again, the supernatant was completely removed. To the resulting pellet, 1 ml of MT medium as added, and the pellet was completely suspended using a micropipette, followed by shake culture at 37° C. at 200 rpm for 1 hour. The culture liquid was plated on an MTNm plate, and static culture was carried out at 37° C. overnight, to obtain transformed Brevibacillus.

(2) Protein Expression Culture of *Brevibacillus*

A single colony of the transformed *Brevibacillus* was smeared on an MTNm plate, and left to stand at 30° C. overnight to perform culture. Subsequently, bacterial cells were scraped with a 1-µl sterile disposable loop from the plate medium after the culture, and then inoculated into 5 ml of TMNm medium preliminarily dispensed in a sterile 50-ml polystyrene tube. Shake culture was then carried out at 30° C. at 120 rpm for 48 hours. After completion of the culture, the culture liquid containing bacterial cells was sampled.

The culture liquid containing bacterial cells was aliquoted in 100-µl volumes into 1.5-ml Eppendorf tubes, and centrifuged (8,000× g, 4° C., 10 minutes) to separate the bacterial cells from the culture supernatant, followed by storing 50 µl of the culture supernatant and the whole amount of bacterial cells at −80° C.

(3) Extraction of Protein from *Brevibacillus*

To 50 µl of the cryopreserved culture supernatant, 50 µl of 2×sample buffer (EZ Apply, manufactured by ATTO) was added, and the resulting mixture was stirred using a vortex mixer, followed by heating the mixture in boiling water for 10 minutes to perform SDS treatment.

On the other hand, the bacterial cells were homogenized in 100 µl of xTractor Buffer (Takara Bio Inc.) containing 0.01% SEM-nuclease (Wako), and then centrifuged at 10,000×g for 10 minutes at 4° C. Thereafter, 50 µl of 2× sample buffer was added to 50 µl of the supernatant fraction (intracellular soluble fraction), and SDS treatment was carried out by the same procedure.

(4) Western Analysis

As a standard substance for protein quantification, an esterase (EstA) preparation was used. By 2-fold serial dilution of the preparation with a sample buffer, a dilution series to be used as standards was prepared.

For electrophoresis (SDS-PAGE) of protein, an electrophoresis tank (Criterion cell, BIO RAD) and Criterion TGX-gel (BIO RAD) were used. In the electrophoresis tank, an electrophoresis buffer (Tris/Glycine/SDS Buffer, BIO RAD) was placed, and 4 µl of the SDS-treated sample was applied to each well, followed by performing electrophoresis at a constant voltage of 200 V for 40 minutes.

The gel after the electrophoresis was subjected to blotting by Trans-Blot Turbo (BIO RAD) using a Trans-Blot Transfer Pack (BIO RAD).

The membrane after the blotting was immersed in a blocking solution (TBS system, pH 7.2; Nacalai Tesque, Inc.), and shaken at room temperature for 1 hour or left to stand at 4° C. for 16 hours. Thereafter, the membrane was washed by three times of shaking in TBS-T (137 mM sodium chloride, 2.68 mM potassium chloride, 1% polyoxyethylene sorbitan monolaurate, 25 mM Tris-HCl, pH 7.4) at room temperature for 5 minutes.

For detection of esterase, an antiserum Mouse-monoclonal Anti-6×His antibody (Abcam) diluted 6,000-fold with TBS-T was used. The membrane was immersed in the dilution, and shaken at room temperature for 2 hours to allow antigen-antibody reaction, followed by three times of washing by shaking in TBS-T at room temperature for 5 minutes. As a secondary antibody, an Anti-Mouse IgG, AP-linked Antibody (Cell Signaling TECHNOLOGY) diluted 3000-fold with TBS-T was used.

The membrane was immersed in the dilution, and shaken at room temperature for 1 hour to allow antigen-antibody reaction, followed by three times of washing by shaking in TBS-T at room temperature for 5 minutes. Chromogenic reaction with alkaline phosphatase was carried out by immersing the membrane in a coloring solution (0.1 M sodium chloride, 5 mM magnesium chloride, 0.33 mg/ml nitroblue tetrazolium, 0.33 mg/ml 5-bromo-4-chloro-3-indolyl-phosphate, 0.1 M Tris-HCl, pH 9.5), and shaking the membrane at room temperature for 15 minutes. The membrane was washed with distilled water, and then dried at normal temperature.

From the membrane after the coloring, an image was obtained using a scanner (PM-A900, Epson) at a resolution of 600 dpi, and esterase in the culture supernatant and in the bacterial cell-solubilized fraction was quantified using image analysis software (CS Analyzer ver. 3.0, Atto Corporation). The total amount of the enzyme in the culture supernatant and in the bacterial cell-solubilized fraction was regarded as the total amount of solubilized esterase, and subjected to comparison.

(5) Providing of Cultured Sample for Enzyme Purification

The *Brevibacillus* strain constructed for esterase expression, stored at −80° C., was smeared on an MTNm plate using a sterile loop, and cultured at 37° C. for 16 to 20 hours. Subsequently, 5 ml of TMNm was dispensed into a 50-ml polypropylene conical tube, and the plate sample was inoculated thereto with a sterile loop. After performing shake culture at 30° C. at 120 rpm for 16 to 20 hours, the whole amount of the culture was added to a 500-ml baffled Erlenmeyer flask containing 150 ml of TMNm medium dispensed therein, and shake culture was carried out at 120 rpm at 30° C. for 48 hours. Into a 50-ml polypropylene conical tube, 50 ml of the culture was taken, and centrifugation was carried out at 8,000×g for 10 minutes at 4° C. After precipitation of the bacterial cells, 40 ml of the supernatant was transferred to another tube, and the remaining supernatant was completely removed with a pipet. The tubes each containing the supernatant or the bacterial cells (precipitate) were frozen with liquid nitrogen, and then stored at −80° C.

(6) Purification of His-Tag Fusion Enzyme Protein from Supernatant Fraction

After thawing 40 ml of the supernatant fraction cryopreserved at −80° C., 13.3 ml of 0.4 M sodium phosphate buffer (pH 7.4) containing 1.2 M NaCl and 0.04 M imidazole was added thereto and mixed therewith. An EcoPack column (BIO RAD) was packed with 5 ml of TALON His-tag fusion protein purification resin (Clontech), and then equilibrated with 25 ml of an equilibration buffer (0.1 M sodium phosphate buffer (pH 7.4) containing 0.3 M NaCl and 0.01 M imidazole). About 10 ml of the supernatant sample prepared with phosphate buffer was charged into the column, and the resin was suspended therein. Using the remaining sample, the whole amount of the resin was washed out into a 100-ml polypropylene centrifuge tube (manufactured by IWAKI). The centrifuge tube containing the sample was placed on a rotator, and the His-tag fusion enzyme protein was allowed to adsorb to the resin for 2 hours in a low-temperature chamber (4° C.).

Subsequently, the resin to which the sample was adsorbed, suspended in a sample buffer, was transferred to an empty column, and only the buffer was eluted therefrom. Further, the resin was washed by allowing 50 ml of the equilibration buffer to flow through the column.

Thereafter, the His-tag fusion enzyme protein adsorbed to the resin was eluted using 20 ml of an elution buffer (0.1 M sodium phosphate buffer (pH 7.4) containing 0.3 M NaCl and 0.15 M imidazole). The elution was carried out by repeating 10 times an operation of taking a 2-ml fraction into a 2-ml Eppendorf tube ice-cooled on an aluminum block, to obtain 10 tubes containing separate fractions. Twenty microliters of each fraction was taken into a 1.5-ml Eppendorf tube, and 20 µl of 2×sample buffer (EZ Apply, manufactured by ATTO) was added thereto, followed by stirring the resulting mixture using a vortex mixer, and heating the mixture in boiling water for 10 minutes to perform SDS treatment of the sample.

(7) Purification of His-Tag Fusion Enzyme Protein from Bacterial Cell Fraction

After thawing the bacterial cell fraction cryopreserved at −80° C., 50 ml of xTractor buffer (Clonthech) containing 5 µl of SEM nuclease (manufactured by Wako) was added thereto, and the resulting mixture was shaken for about 20 minutes at room temperature, to solubilize the bacterial cells. Similarly to the case of the supernatant sample, an EcoPack column (BIO RAD) was packed with 5 ml of TALON His-tag fusion protein purification resin (Clontech), and then purification of His-tag fusion enzyme protein was carried out by the the same method. Twenty microliters of each fraction was taken into a 1.5-ml Eppendorf tube, and 20 µl of 2×sample buffer (EZ Apply, manufactured by ATTO) was added thereto, followed by stirring the resulting mixture using a vortex mixer, and heating the mixture in boiling water for 10 minutes to perform SDS treatment of the sample.

(8) Western Analysis of Purified Fractions

As a standard substance for protein quantification, a purified esterase (EstA) preparation was used similarly to the case of quantification for the crude extract fraction. By 2-fold serial dilution of the preparation with a sample buffer, a dilution series to be used as standards was prepared. For electrophoresis (SDS-PAGE) of protein, an electrophoresis tank (Criterion cell, BIO RAD) and Criterion TGX-gel (BIO RAD) were used. In the electrophoresis tank, an electrophoresis buffer (Tris/Glycine/SDS Buffer, BIO RAD) was placed, and 4 µl of the SDS-treated fraction sample was applied to each well, followed by performing electrophoresis at a constant voltage of 200 V for 40 minutes.

The gel after the electrophoresis was subjected to blotting by Trans-Blot Turbo (BIO RAD) using a Trans-Blot Transfer Pack (BIO RAD).

The operation after the blotting was carried out by the same method as in the Western analysis of the crude extract sample described above.

(9) Ultrafiltration and Concentration of Purified His-Tag Fusion Enzyme Protein

The fractions for which the presence of the enzyme protein of interest could be confirmed by the Western analysis described above were combined together, and transferred to a centrifugal filtration unit (Amicon Ultra-10 K, Merck), followed by carrying out ultrafiltration at 5,000×g for 30 minutes at 4° C. Subsequently, the filtrate was discarded, and 10 ml of 1×PBS buffer (pH 7.4) was added, followed by carrying out ultrafiltration by the same method as described above. The same operation was further repeated three times, and the sample was concentrated to about 1.0 ml to remove imidazole in the sample. The enzyme protein concentration in the concentrate was determined by the Bradford method using BSA as a standard substance.

(10) Measurement of Esterase Activity

The activity of esterase was measured by the following method using a Lipase Kit S manufactured by DS Pharma Biomedical Co., Ltd.

First, 2.4 ml of the included buffer was added to the coloring-agent container. After allowing complete dissolution, 22 ml of distilled water was added thereto to obtain a coloring stock solution. The coloring stock solution prepared was aliquoted in 1.1-ml volumes into 1.5-ml Eppendorf tubes, and cryopreserved at −20° C.

Subsequently, the included reaction stop stock solution was incubated at 30° C. for 5 to 10 minutes to allow thawing, and the whole amount of the solution was diluted with distilled water to a final volume of 500 ml. The resulting dilution was stored in a refrigerator at 4° C. Immediately before the activity measurement, 1.1 ml of the coloring stock solution was thawed, and 1.1 ml of the included buffer and 8.8 ml of distilled water were added thereto, to prepare a coloring solution.

Subsequently, for 100 µl of the coloring solution, 5 µl of the esterase sample for measurement was dispensed into a 96-well microplate, and the resulting mixture was mixed using a vortex mixer, followed by adding 10 µl of the included substrate solution (BALB) to each well, and mixing the resulting mixture. The plate was then covered with aluminum foil, and enzyme reaction was carried out at 30° C. for 30 minutes under dark conditions. Thereafter, 150 µl of the reaction stop solution, preliminarily incubated at 30° C., was added thereto to stop the reaction. As a blank, a sample series to which the substrate was added after the reaction was provided. The absorbances (412 nm) of both samples were measured using a microplate reader, and the value after subtraction of the blank value was multiplied by 1000 to obtain the BALB unit value, which was used as an index of enzyme activity.

(11) Evaluation with Yeast *S. cerevisiae*

By the method described in FIG. 2 of WO2017/115853, each transformed yeast, in which a plasmid encoding a fusion protein composed of human growth hormone protein (hGH) and a peptide tag added to the N-terminus thereof was introduced, was cultured, and 200 µl of the resulting culture was taken into a 1.5-ml Eppendorf tube. Thereafter, the tube was centrifuged at 2,000×g at 4° C. for 5 minutes, and then the supernatant was discarded, followed by freezing the precipitate (yeast cells) with liquid nitrogen and storing the precipitate at −80° C. Subsequently, the precipitate was thawed on ice, and the cell cluster was broken by vortexing. Thereafter, 0.5 ml of Yeast PreLysis buffer (manufactured by Atto Corporation) containing complete ULTRA cocktail (manufactured by Merck) and 0.1 µg/ml SEM nuclease (manufactured by Fujifilm Wako Pure Chemical Corporation) was added to the cells, and the cells were left to stand at room temperature for 10 minutes. Subsequently, the cell lysate was centrifuged at 10,000×g at 4° C. for 10 minutes to obtain the centrifugation supernatant and precipitate as a soluble fraction and insoluble fraction, respectively. After carrying out SDS treatment by a predetermined method, electrophoresis was carried out by SDS-PAGE, and then Western analysis was carried out to measure the amount of hGH in each fraction.

<Results>

Figure 3:
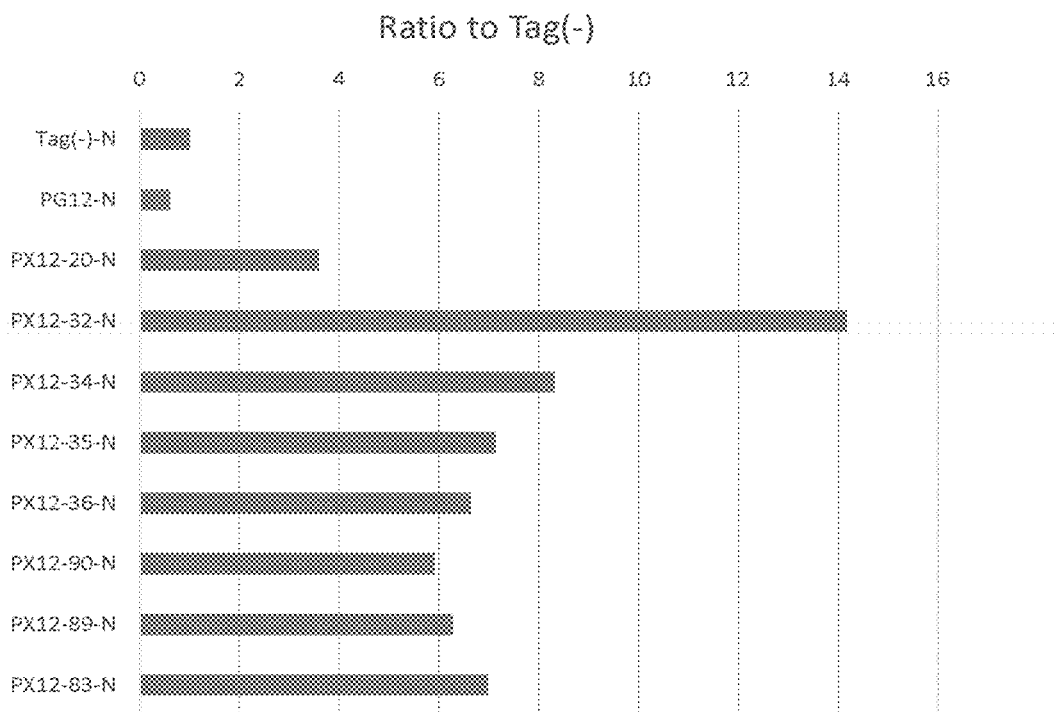
FIG. 3 is a graph illustrating comparison of the expression level of esterase having each peptide tag linked to the N-terminal side thereof, in a soluble fraction.

(1) Improvement of Protein Expression Level in Soluble Fraction in *Brevibacillus* by Addition of Various Peptide Tags to N-Terminus The prepared recombinant *Brevibacillus* was cultured under predetermined conditions, and esterase was extracted therefrom under predetermined conditions, followed by measuring the expression level of the enzyme in the soluble fraction by Western analysis. As a result, as shown in FIG. 3, when PG12 (SEQ ID NO:1) was added to the N-terminus in Comparative Example 2, no improvement of esterase expression was found in the soluble fraction relative to the case without addition of a tag. When PX12-20 was added to the N-terminus in Comparative Example 3, the expression level was 3.6 times higher than that in the case without addition of a tag. In contrast, when PX12-32, PX12-33, PX12-34, PX12-35, PX12-36, PX12-90, PX12-89, or PX12-

83 was added to the N-terminus of esterase, expression levels not less than 6 times higher than that in the case without addition of a tag were obtained, indicating that they are superior to the Comparative Examples. A particularly higher productivity was obtained when PX12-32 was added to the N-terminus.

Figure 4:
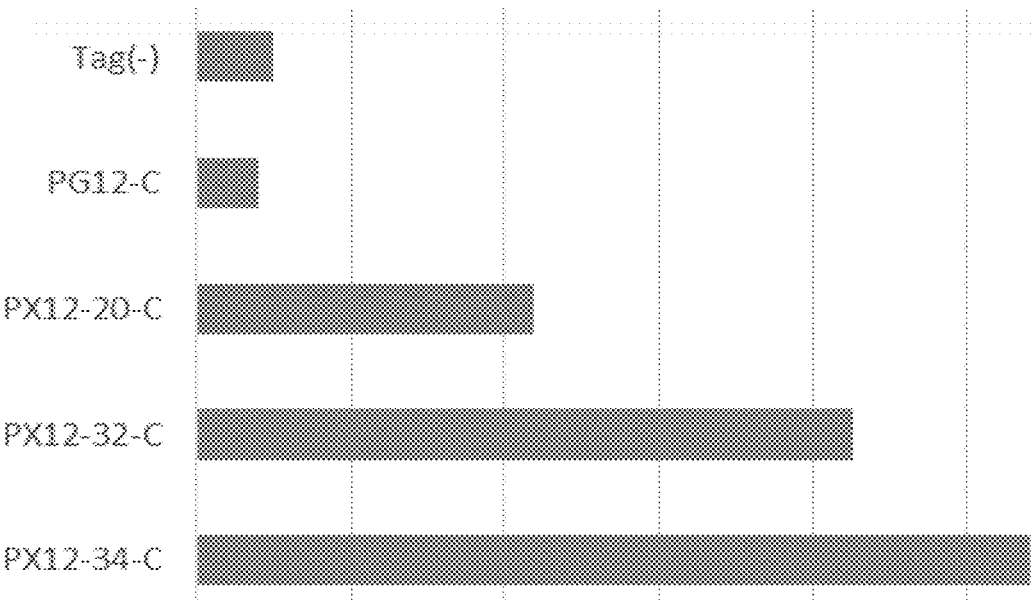
FIG. 4 is a graph illustrating comparison of the expression level of esterase having each peptide tag linked to the C-terminal side thereof, in a soluble fraction.

(2) Improvement of Protein Expression Level in Soluble Fraction in *Brevibacillus* by Addition of Various Peptide Tags to C-Terminus The prepared recombinant *Brevibacillus* was cultured under predetermined conditions, and esterase was extracted therefrom under predetermined conditions, followed by measuring the expression level of the enzyme in the soluble fraction by Western analysis. As a result, as shown in FIG. 4, when PG12 (SEQ ID NO:1) was added to the C-terminus in Comparative Example 5, no improvement of esterase expression was found in the soluble fraction relative to the case without addition of a tag. When PX12-20 was added to the C-terminus in Comparative Example 6, the expression level was about 4 times higher than that in the case without addition of a tag. In contrast, when PX12-32 or PX12-34 was added to the C-terminus of esterase, expression levels not less than 8 times higher than that in the case without addition of a tag were obtained, clearly indicating that they result in higher production of esterase in the soluble fraction even compared to Comparative Example 6 (addition of PX12-20).

(3) Influence of Addition of Various Peptide Tags on Esterase Activity

Figure 5:
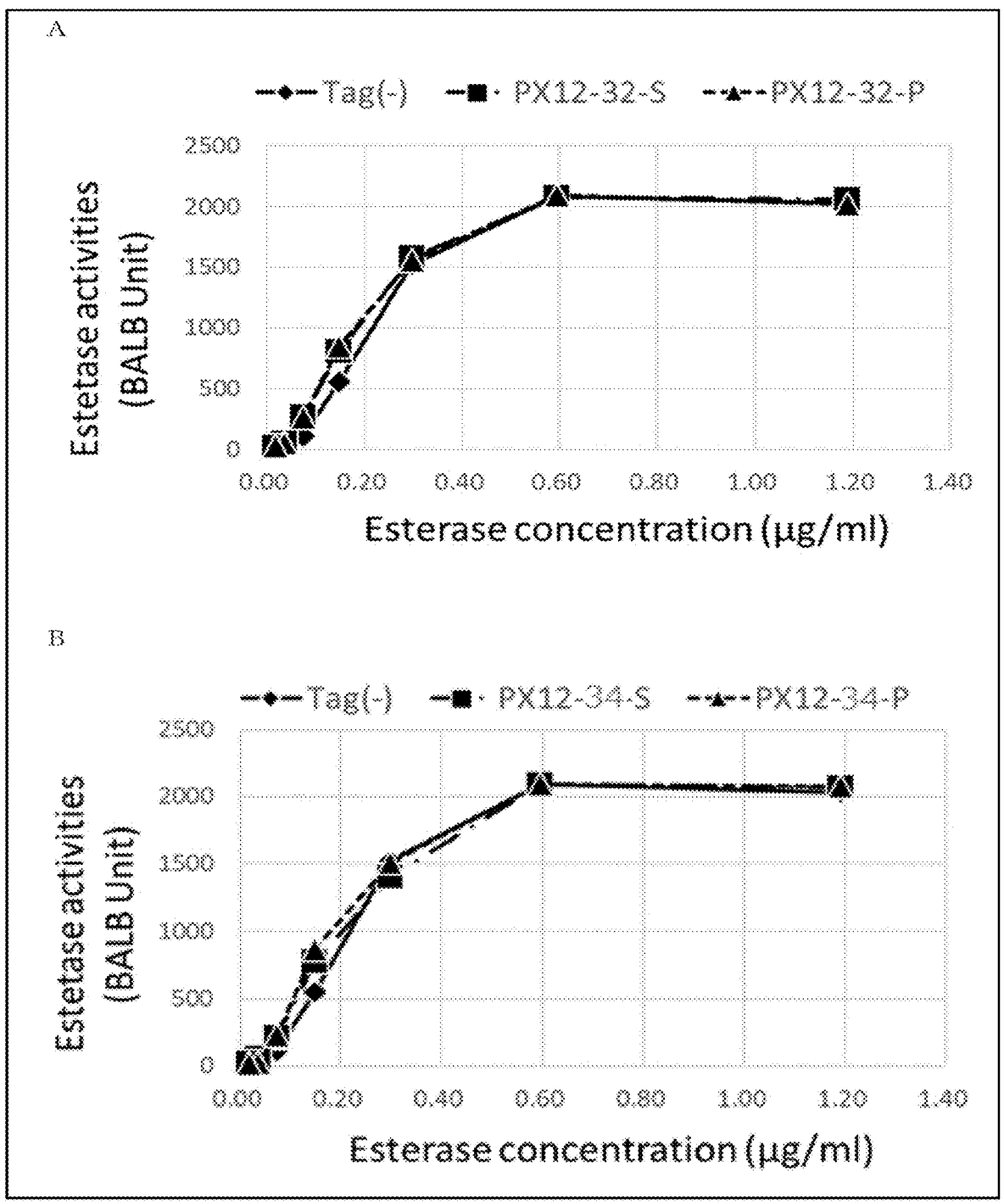
FIG. 5 is a graph illustrating the result of comparison of the activity of esterase having a tag (A: PX12-32, B: PX12-34) added thereto. S represents a fraction secreted into the medium, and P represents a soluble fraction in the cell.

The prepared recombinant *Brevibacillus* was cultured under predetermined conditions, and esterase secreted into the medium and esterase in the soluble fraction in the bacterial cells were purified under predetermined conditions, followed by investigation of the influence of the addition of each tag on the enzyme activity. As a result, as shown in FIG. 5, N-terminal-tagged esterases secreted into the medium (PX12-32-S and PX12-34-S) were found to have the same activity as that of the non-tagged (Tag(–)) esterase. Further, N-terminal-tagged esterases obtained by homogenization of the bacterial cells (PX12-32-P and PX12-34-P) were also found to have the same activity as that of the non-tagged (Tag(–)) esterase.

Figure 6:
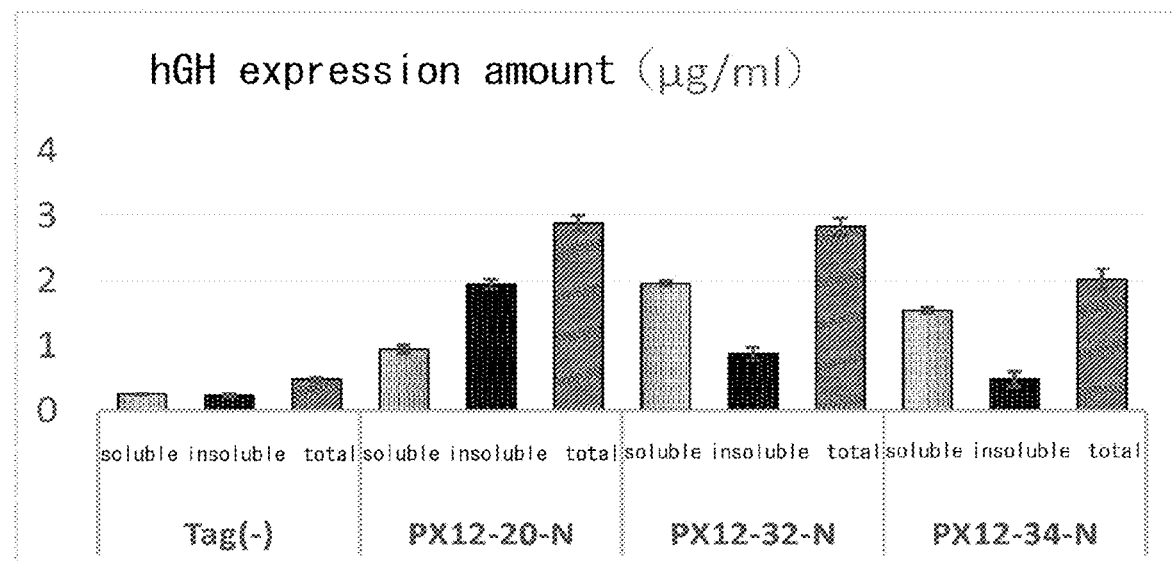
FIG. 6 is a graph illustrating comparison of the expression level of human growth hormone having various peptide tags linked to the N-terminal side thereof, which comparison was made for each fraction (yeast).

(4) Improvement of Protein Expression Level in Soluble Fraction in Yeast by Addition of Various Peptide Tags to N-Terminus The prepared recombinant yeast was cultured, and the expression level of hGH in each fraction was measured by Western analysis. As a result, as shown in FIG. 6, when PX12-20-N was added to the N-terminus, the amount of hGH was smaller in the soluble fraction than in the insoluble fraction. However, when PX12-32 or PX12-34 was added to the N-terminus of hGH, the expression level of hGH in the soluble fraction remarkably increased. Thus, it was found that effective improvement of the protein expression level in the soluble fraction can be achieved also in eukaryotic cells.

By the linking of a peptide tag containing a particular sequence, effective suppression of degradation of a fusion protein can be expected in eukaryotes.

The invention claimed is:

1. A soluble fraction prepared by an expression system comprising a polynucleotide introduced in the expression system, wherein the polynucleotide encodes a fusion protein and comprises:
    a protein of interest; and
    a peptide tag linked to the protein of interest and comprising the following amino acid sequence:
        X(PY)$_q$PZ,
    wherein
        P represents proline;
        X represents an amino acid sequence composed of 0 to 5 amino acids independently selected from the group consisting of arginine (R), glycine (G), serine(S), lysine (K), threonine (T), leucine (L), asparagine (N), glutamine (Q), and methionine (M);
        Y represents an amino acid sequence composed of 1 to 4 amino acids independently selected from the group consisting of G, T, Q, and M;
        q represents an integer of 1 to 10; and
        Z represents an amino acid sequence composed of 0 to 10 amino acids independently selected from the group consisting of R, G, S, K, T, L, N, Q, and M;
        with the proviso that the amino acid sequence of the peptide tag comprises at least three Qs, Ms, Ls, Ns, and/or Ts in total;
    wherein the soluble fraction comprises the fusion protein produced and accumulated from the polynucleotide, and
    wherein PY is at least one selected from the group consisting of PGM, PGT, PQQ, PGMG, PGTG, and PQQQ.

2. The soluble fraction according to claim 1, wherein the peptide tag has a length of from 10 to 30 amino acids.

3. The soluble fraction according to claim 1, wherein the protein of interest is an enzyme.

4. The soluble fraction according to any one of claim 1, wherein the fusion protein comprises a secretion signal.

5. The soluble fraction according to claim 1, wherein the peptide tag is linked to a C-terminal side of the protein of interest.

6. A method of producing a fusion protein, the method comprising collecting the soluble fraction according to claim 1, and extracting the fusion protein.

7. The soluble fraction according to claim 1, wherein the peptide tag has the amino acid sequence of SEQ ID NO: 12, 15, 19, or 23.

8. A soluble fraction prepared by an expression system comprising a polynucleotide introduced in the expression system, wherein the polynucleotide encodes a fusion protein and comprises:
    a protein of interest; and
    a peptide tag linked to the protein of interest and comprising the amino acid sequence of SEQ ID NO: 12, 15, 19, 21, or 23;
    wherein the soluble fraction comprises the fusion protein produced and accumulated from the polynucleotide.

* * * * *

SEQUENCE LISTING

```
<160> NUMBER OF SEQ ID NOS: 242

<210> SEQ ID NO 1
<211> LENGTH: 12
<212> TYPE: PRT
<213> ORGANISM: Artificial Sequence
<220> FEATURE:
<223> OTHER INFORMATION: Synthetic Peptide PG12

<400> SEQUENCE: 1

Arg Ser Pro Gly Ser Gly Pro Gly Ser Pro Arg Ser
1               5                   10

<210> SEQ ID NO 2
<211> LENGTH: 90
<212> TYPE: DNA
<213> ORGANISM: Artificial Sequence
<220> FEATURE:
<223> OTHER INFORMATION: Synthetic DNA mCWSP-AD-PG12-BsestAF

<400> SEQUENCE: 2
acttactgtt gctcccatgg ctttcgctgc agatagaaaa cctggtaaag gtcctggtaa      60
acctagatcc gctgaacaca atccagtcgt                                      90

<210> SEQ ID NO 3
<211> LENGTH: 83
<212> TYPE: DNA
<213> ORGANISM: Artificial Sequence
<220> FEATURE:
<223> OTHER INFORMATION: Synthetic DNA BsestAR-PG12-stopXt

<400> SEQUENCE: 3
cctccgcact ataatgccga agctttcagg aacgtgggga acctggaccg gaacctgggg      60
```

```
aacgattcgt attctggccc ccg                                              83

<210> SEQ ID NO 4
<211> LENGTH: 12
<212> TYPE: PRT
<213> ORGANISM: Artificial Sequence
<220> FEATURE:
<223> OTHER INFORMATION: Synthetic Peptide PX12-20

<400> SEQUENCE: 4

Arg Lys Pro Gly Lys Gly Pro Gly Lys Pro Arg Ser
1               5                   10

<210> SEQ ID NO 5
<211> LENGTH: 89
<212> TYPE: DNA
<213> ORGANISM: Artificial Sequence
<220> FEATURE:
<223> OTHER INFORMATION: Synthetic DNA mCWSP-AD-PX12-20-BsestAF

<400> SEQUENCE: 5
acttactgtt gctcccatgg ctttcgctgc agatcgtaaa ccaggtaaag gtccaggtaa     60
accacgttcc gctgaacaca atccagtcg                                       89

<210> SEQ ID NO 6
<211> LENGTH: 83
<212> TYPE: DNA
<213> ORGANISM: Artificial Sequence
<220> FEATURE:
<223> OTHER INFORMATION: Synthetic DNA BsestAR-PX12-20-stopXt

<400> SEQUENCE: 6
cctccgcact ataatgccga agctttcagg aacgtggttt acctggacct ttacctggtt     60
tacgattcgt attctggccc ccg                                              83

<210> SEQ ID NO 7
<211> LENGTH: 12
<212> TYPE: PRT
<213> ORGANISM: Artificial Sequence
<220> FEATURE:
<223> OTHER INFORMATION: Synthetic Peptide PX12-32

<400> SEQUENCE: 7

Arg Gln Pro Gly Gln Gly Pro Gly Gln Pro Arg Ser
1               5                   10

<210> SEQ ID NO 8
<211> LENGTH: 89
<212> TYPE: DNA
<213> ORGANISM: Artificial Sequence
<220> FEATURE:
<223> OTHER INFORMATION: Synthetic DNA mCWSP-AD-PX12-32-BsestAF

<400> SEQUENCE: 8
acttactgtt gctcccatgg ctttcgctgc agatcgtcaa ccaggtcaag gtccaggtca     60
accacgttcc gctgaacaca atccagtcg                                       89

<210> SEQ ID NO 9
<211> LENGTH: 83
<212> TYPE: DNA
<213> ORGANISM: Artificial Sequence
<220> FEATURE:
<223> OTHER INFORMATION: Synthetic DNA BsestAR-PX12-32-stopXt
```

```
<400> SEQUENCE: 9
cctccgcact ataatgccga agctttcagg aacgtggttg acctggacct tgacctggtt    60
gacgattcgt attctggccc ccg                                            83

<210> SEQ ID NO 10
<211> LENGTH: 12
<212> TYPE: PRT
<213> ORGANISM: Artificial Sequence
<220> FEATURE:
<223> OTHER INFORMATION: Synthetic Peptide PX12-33

<400> SEQUENCE: 10

Arg Asn Pro Gly Asn Gly Pro Gly Asn Pro Arg Ser
1               5                   10

<210> SEQ ID NO 11
<211> LENGTH: 89
<212> TYPE: DNA
<213> ORGANISM: Artificial Sequence
<220> FEATURE:
<223> OTHER INFORMATION: Synthetic DNA mCWSP-AD-PX12-33-BsestAF

<400> SEQUENCE: 11
acttactgtt gctcccatgg ctttcgctgc agatcgtaac ccaggtaacg gtccaggtaa    60
cccacgttcc gctgaacaca atccagtcg                                      89

<210> SEQ ID NO 12
<211> LENGTH: 12
<212> TYPE: PRT
<213> ORGANISM: Artificial Sequence
<220> FEATURE:
<223> OTHER INFORMATION: Synthetic Peptide PX12-34

<400> SEQUENCE: 12

Arg Met Pro Gly Met Gly Pro Gly Met Pro Arg Ser
1               5                   10

<210> SEQ ID NO 13
<211> LENGTH: 89
<212> TYPE: DNA
<213> ORGANISM: Artificial Sequence
<220> FEATURE:
<223> OTHER INFORMATION: Synthetic DNA mCWSP-AD-PX12-34-BsestAF

<400> SEQUENCE: 13
acttactgtt gctcccatgg ctttcgctgc agatcgtatg ccaggtatgg gtccaggtat    60
gccacgttcc gctgaacaca atccagtcg                                      89

<210> SEQ ID NO 14
<211> LENGTH: 83
<212> TYPE: DNA
<213> ORGANISM: Artificial Sequence
<220> FEATURE:
<223> OTHER INFORMATION: Synthetic DNA BsestAR-PX12-34-stopXt

<400> SEQUENCE: 14
cctccgcact ataatgccga agctttcagg aacgtggcat acctggaccc atacctggca    60
tacgattcgt attctggccc ccg                                            83

<210> SEQ ID NO 15
<211> LENGTH: 12
<212> TYPE: PRT
<213> ORGANISM: Artificial Sequence
```

```
<220> FEATURE:
<223> OTHER INFORMATION: Synthetic Peptide PX12-35

<400> SEQUENCE: 15

Arg Thr Pro Gly Thr Gly Pro Gly Thr Pro Arg Ser
1               5                   10

<210> SEQ ID NO 16
<211> LENGTH: 89
<212> TYPE: DNA
<213> ORGANISM: Artificial Sequence
<220> FEATURE:
<223> OTHER INFORMATION: Synthetic DNA mCWSP-AD-PX12-35-BsestAF

<400> SEQUENCE: 16
acttactgtt gctcccatgg ctttcgctgc agatcgtact ccaggtactg gtccaggtac      60
tccacgttcc gctgaacaca atccagtcg                                       89

<210> SEQ ID NO 17
<211> LENGTH: 12
<212> TYPE: PRT
<213> ORGANISM: Artificial Sequence
<220> FEATURE:
<223> OTHER INFORMATION: Synthetic Peptide PX12-36

<400> SEQUENCE: 17

Arg Leu Pro Gly Leu Gly Pro Gly Leu Pro Arg Ser
1               5                   10

<210> SEQ ID NO 18
<211> LENGTH: 89
<212> TYPE: DNA
<213> ORGANISM: Artificial Sequence
<220> FEATURE:
<223> OTHER INFORMATION: Synthetic DNA mCWSP-AD-PX12-36-BsestAF

<400> SEQUENCE: 18
acttactgtt gctcccatgg ctttcgctgc agatcgtctg ccaggtctgg gtccaggtct      60
gccacgttcc gctgaacaca atccagtcg                                       89

<210> SEQ ID NO 19
<211> LENGTH: 12
<212> TYPE: PRT
<213> ORGANISM: Artificial Sequence
<220> FEATURE:
<223> OTHER INFORMATION: Synthetic Peptide PX12-83

<400> SEQUENCE: 19

Arg Met Pro Gly Met Pro Gly Met Pro Gly Arg Ser
1               5                   10

<210> SEQ ID NO 20
<211> LENGTH: 89
<212> TYPE: DNA
<213> ORGANISM: Artificial Sequence
<220> FEATURE:
<223> OTHER INFORMATION: Synthetic DNA mCWSP-AD-PX12-83-BsestAF

<400> SEQUENCE: 20
acttactgtt gctcccatgg ctttcgctgc agatcgtatg ccaggtatgc caggtatgcc      60
aggtcgttcc gctgaacaca atccagtcg                                       89

<210> SEQ ID NO 21
<211> LENGTH: 12
```

```
<212> TYPE: PRT
<213> ORGANISM: Artificial Sequence
<220> FEATURE:
<223> OTHER INFORMATION: Synthetic Peptide PX12-89

<400> SEQUENCE: 21

Arg Gln Pro Gly Gln Gly Pro Gly Gln Gly Arg Ser
1               5                   10

<210> SEQ ID NO 22
<211> LENGTH: 89
<212> TYPE: DNA
<213> ORGANISM: Artificial Sequence
<220> FEATURE:
<223> OTHER INFORMATION: Synthetic DNA mCWSP-AD-PX12-89-BsestAF

<400> SEQUENCE: 22
acttactgtt gctcccatgg ctttcgctgc agatcgtcaa ccaggtcaag gtccaggtca      60
aggtcgttcc gctgaacaca atccagtcg                                        89

<210> SEQ ID NO 23
<211> LENGTH: 12
<212> TYPE: PRT
<213> ORGANISM: Artificial Sequence
<220> FEATURE:
<223> OTHER INFORMATION: Synthetic Peptide PX12-90

<400> SEQUENCE: 23

Arg Gln Pro Gln Gln Gln Pro Gln Gln Pro Arg Ser
1               5                   10

<210> SEQ ID NO 24
<211> LENGTH: 89
<212> TYPE: DNA
<213> ORGANISM: Artificial Sequence
<220> FEATURE:
<223> OTHER INFORMATION: Synthetic DNA mCWSP-AD-PX12-90-BsestAF

<400> SEQUENCE: 24
acttactgtt gctcccatgg ctttcgctgc agatcgtcaa ccacaacaac aaccacaaca      60
accacgttcc gctgaacaca atccagtcg                                        89

<210> SEQ ID NO 25
<211> LENGTH: 181
<212> TYPE: PRT
<213> ORGANISM: Bacillus subtilis

<400> SEQUENCE: 25

Ala Glu His Asn Pro Val Val Met Val His Gly Ile Gly Gly Ala Ser
1               5                   10                  15

Phe Asn Phe Ala Gly Ile Lys Ser Tyr Leu Val Ser Gln Gly Trp Ser
            20                  25                  30

Arg Asp Lys Leu Tyr Ala Val Asp Phe Trp Asp Lys Thr Gly Thr Asn
        35                  40                  45

Tyr Asn Asn Gly Pro Val Leu Ser Arg Phe Val Gln Lys Val Leu Asp
    50                  55                  60

Glu Thr Gly Ala Lys Lys Val Asp Ile Val Ala His Ser Met Gly Gly
65                  70                  75                  80

Ala Asn Thr Leu Tyr Tyr Ile Lys Asn Leu Asp Gly Gly Asn Lys Val
                85                  90                  95

Ala Asn Val Val Thr Leu Gly Gly Ala Asn Arg Leu Thr Thr Gly Lys
            100                 105                 110
```

Ala Leu Pro Gly Thr Asp Pro Asn Gln Lys Ile Leu Tyr Thr Ser Ile
            115                 120                 125

Tyr Ser Ser Ala Asp Met Ile Val Met Asn Tyr Leu Ser Arg Leu Asp
    130                 135                 140

Gly Ala Arg Asn Val Gln Ile His Gly Val Gly His Ile Gly Leu Leu
145                 150                 155                 160

Tyr Ser Ser Gln Val Asn Ser Leu Ile Lys Glu Gly Leu Asn Gly Gly
                165                 170                 175

Gly Gln Asn Thr Asn
            180

<210> SEQ ID NO 26
<211> LENGTH: 543
<212> TYPE: DNA
<213> ORGANISM: Bacillus subtilis

<400> SEQUENCE: 26
gctgaacaca atccagtcgt tatggttcac ggtattggag gggcatcatt caattttgcg      60
ggaattaaga gctatctcgt atctcagggc tggtcgcggg acaagctgta tgcagttgat     120
ttttgggaca agacaggcac aaattataac aatggaccgg tattatcacg atttgtgcaa     180
aaggttttag atgaaacggg tgcgaaaaaa gtggatattg tcgctcacag catgggggc      240 gcgaacacac tttactacat aaaaaatctg gacggcggaa ataaagttgc aaacgtcgtg     300
acgcttggcg gcgcgaaccg tttgacgaca ggcaaggcgc ttccgggaac agatccaaat     360
caaaagattt tatacacatc catttacagc agtgccgata tgattgtcat gaattactta     420
tcaagattag atggtgctag aaacgttcaa atccatggcg ttggacacat cggccttctg     480
tacagcagcc aagtcaacag cctgattaaa gaagggctga acggcggggg ccagaatacg     540
aat                                                                   543

<210> SEQ ID NO 27
<211> LENGTH: 6
<212> TYPE: PRT
<213> ORGANISM: Artificial Sequence
<220> FEATURE:
<223> OTHER INFORMATION: Synthetic peptide 6XHis

<400> SEQUENCE: 27

His His His His His His
1               5

<210> SEQ ID NO 28
<211> LENGTH: 18
<212> TYPE: DNA
<213> ORGANISM: Artificial Sequence
<220> FEATURE:
<223> OTHER INFORMATION: Synthetic DNA 6xhis

<400> SEQUENCE: 28
catcaccatc accatcac                                                    18

<210> SEQ ID NO 29
<211> LENGTH: 54
<212> TYPE: DNA
<213> ORGANISM: Artificial Sequence
<220> FEATURE:
<223> OTHER INFORMATION: Synthetic DNA mCWSP-AD-BsestAF

<400> SEQUENCE: 29

-continued acttactgtt gctcccatgg ctttcgctgc agatgctgaa cacaatccag tcgt    54

<210> SEQ ID NO 30
<211> LENGTH: 47
<212> TYPE: DNA
<213> ORGANISM: Artificial Sequence
<220> FEATURE:
<223> OTHER INFORMATION: BsestAR-stopXt

<400> SEQUENCE: 30
cctccgcact ataatgccga agctttcaat tcgtattctg gccccg    47

<210> SEQ ID NO 31
<211> LENGTH: 71
<212> TYPE: DNA
<213> ORGANISM: Artificial Sequence
<220> FEATURE:
<223> OTHER INFORMATION: Synthetic DNA mCWSP-AD-6xHis-BsestAF

<400> SEQUENCE: 31
acttactgtt gctcccatgg ctttcgctgc agatcatcac catcaccatc acgctgaaca    60
caatccagtc g    71

<210> SEQ ID NO 32
<211> LENGTH: 65
<212> TYPE: DNA
<213> ORGANISM: Artificial Sequence
<220> FEATURE:
<223> OTHER INFORMATION: Synthetic DNA BsestAR-6xHis-stopXt

<400> SEQUENCE: 32
cctccgcact ataatgccga agctttcagt gatggtgatg gtgatgattc gtattctggc    60
ccccg    65

<210> SEQ ID NO 33
<211> LENGTH: 12
<212> TYPE: PRT
<213> ORGANISM: Artificial Sequence
<220> FEATURE:
<223> OTHER INFORMATION: Synthetic Peptide Synthetic Peptide 1-1

<400> SEQUENCE: 33

Arg Gln Pro Gly Gln Gly Pro Gly Gln Pro Arg Ser
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Synthetic Peptide 1-2

<400> SEQUENCE: 34

Arg Asn Pro Gly Asn Gly Pro Gly Asn Pro Arg Ser
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Synthetic Peptide 1-3

<400> SEQUENCE: 35

Arg Met Pro Gly Met Gly Pro Gly Met Pro Arg Ser

```
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Synthetic Peptide 1-4

<400> SEQUENCE: 36

Arg Thr Pro Gly Thr Gly Pro Gly Thr Pro Arg Ser
1               5                   10

<210> SEQ ID NO 37
<211> LENGTH: 12
<212> TYPE: PRT
<213> ORGANISM: Artificial Sequence
<220> FEATURE:
<223> OTHER INFORMATION: Synthetic Peptide 1-5

<400> SEQUENCE: 37

Arg Leu Pro Gly Leu Gly Pro Gly Leu Pro Arg Ser
1               5                   10

<210> SEQ ID NO 38
<211> LENGTH: 12
<212> TYPE: PRT
<213> ORGANISM: Artificial Sequence
<220> FEATURE:
<223> OTHER INFORMATION: Synthetic Peptide 1-6

<400> SEQUENCE: 38

Arg Gln Pro Gly Gln Gly Pro Gly Asn Pro Arg Ser
1               5                   10

<210> SEQ ID NO 39
<211> LENGTH: 12
<212> TYPE: PRT
<213> ORGANISM: Artificial Sequence
<220> FEATURE:
<223> OTHER INFORMATION: Synthetic Peptide 1-7

<400> SEQUENCE: 39

Arg Gln Pro Gly Asn Gly Pro Gly Gln Pro Arg Ser
1               5                   10

<210> SEQ ID NO 40
<211> LENGTH: 12
<212> TYPE: PRT
<213> ORGANISM: Artificial Sequence
<220> FEATURE:
<223> OTHER INFORMATION: Synthetic Peptide 1-8

<400> SEQUENCE: 40

Arg Gln Pro Gly Asn Gly Pro Gly Asn Pro Arg Ser
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Synthetic Peptide 1-9

<400> SEQUENCE: 41

Arg Gln Pro Gly Gln Gly Pro Gly Met Pro Arg Ser
1               5                   10
```

<210> SEQ ID NO 42
<211> LENGTH: 12
<212> TYPE: PRT
<213> ORGANISM: Artificial Sequence
<220> FEATURE:
<223> OTHER INFORMATION: Synthetic Peptide 1-10

<400> SEQUENCE: 42

Arg Gln Pro Gly Met Gly Pro Gly Gln Pro Arg Ser
1               5                   10

<210> SEQ ID NO 43
<211> LENGTH: 12
<212> TYPE: PRT
<213> ORGANISM: Artificial Sequence
<220> FEATURE:
<223> OTHER INFORMATION: Synthetic Peptide 1-11

<400> SEQUENCE: 43

Arg Gln Pro Gly Met Gly Pro Gly Met Pro Arg Ser
1               5                   10

<210> SEQ ID NO 44
<211> LENGTH: 12
<212> TYPE: PRT
<213> ORGANISM: Artificial Sequence
<220> FEATURE:
<223> OTHER INFORMATION: Synthetic Peptide 1-12

<400> SEQUENCE: 44

Arg Gln Pro Gly Gln Gly Pro Gly Thr Pro Arg Ser
1               5                   10

<210> SEQ ID NO 45
<211> LENGTH: 12
<212> TYPE: PRT
<213> ORGANISM: Artificial Sequence
<220> FEATURE:
<223> OTHER INFORMATION: Synthetic Peptide 1-13

<400> SEQUENCE: 45

Arg Gln Pro Gly Thr Gly Pro Gly Gln Pro Arg Ser
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Synthetic Peptide 1-14

<400> SEQUENCE: 46

Arg Gln Pro Gly Thr Gly Pro Gly Thr Pro Arg Ser
1               5                   10

<210> SEQ ID NO 47
<211> LENGTH: 12
<212> TYPE: PRT
<213> ORGANISM: Artificial Sequence
<220> FEATURE:
<223> OTHER INFORMATION: Synthetic Peptide 1-15

<400> SEQUENCE: 47

Arg Gln Pro Gly Gln Gly Pro Gly Leu Pro Arg Ser
1               5                   10

<210> SEQ ID NO 48
<211> LENGTH: 12
<212> TYPE: PRT
<213> ORGANISM: Artificial Sequence
<220> FEATURE:
<223> OTHER INFORMATION: Synthetic Peptide 1-16

<400> SEQUENCE: 48

Arg Gln Pro Gly Leu Gly Pro Gly Gln Pro Arg Ser
1               5                   10

<210> SEQ ID NO 49
<211> LENGTH: 12
<212> TYPE: PRT
<213> ORGANISM: Artificial Sequence
<220> FEATURE:
<223> OTHER INFORMATION: Synthetic Peptide 1-17

<400> SEQUENCE: 49

Arg Gln Pro Gly Leu Gly Pro Gly Leu Pro Arg Ser
1               5                   10

<210> SEQ ID NO 50
<211> LENGTH: 12
<212> TYPE: PRT
<213> ORGANISM: Artificial Sequence
<220> FEATURE:
<223> OTHER INFORMATION: Synthetic Peptide 1-18

<400> SEQUENCE: 50

Arg Asn Pro Gly Asn Gly Pro Gly Gln Pro Arg Ser
1               5                   10

<210> SEQ ID NO 51
<211> LENGTH: 12
<212> TYPE: PRT
<213> ORGANISM: Artificial Sequence
<220> FEATURE:
<223> OTHER INFORMATION: Synthetic Peptide 1-19

<400> SEQUENCE: 51

Arg Asn Pro Gly Gln Gly Pro Gly Asn Pro Arg Ser
1               5                   10

<210> SEQ ID NO 52
<211> LENGTH: 12
<212> TYPE: PRT
<213> ORGANISM: Artificial Sequence
<220> FEATURE:
<223> OTHER INFORMATION: Synthetic Peptide 1-20

<400> SEQUENCE: 52

Arg Asn Pro Gly Gln Gly Pro Gly Gln Pro Arg Ser
1               5                   10

<210> SEQ ID NO 53
<211> LENGTH: 12
<212> TYPE: PRT
<213> ORGANISM: Artificial Sequence
<220> FEATURE:
<223> OTHER INFORMATION: Synthetic Peptide 1-21

<400> SEQUENCE: 53

Arg Asn Pro Gly Asn Gly Pro Gly Met Pro Arg Ser
1               5                   10

```
<210> SEQ ID NO 54
<211> LENGTH: 12
<212> TYPE: PRT
<213> ORGANISM: Artificial Sequence
<220> FEATURE:
<223> OTHER INFORMATION: Synthetic Peptide 1-22

<400> SEQUENCE: 54

Arg Asn Pro Gly Met Gly Pro Gly Asn Pro Arg Ser
1               5                   10

<210> SEQ ID NO 55
<211> LENGTH: 12
<212> TYPE: PRT
<213> ORGANISM: Artificial Sequence
<220> FEATURE:
<223> OTHER INFORMATION: Synthetic Peptide 1-23

<400> SEQUENCE: 55

Arg Asn Pro Gly Met Gly Pro Gly Met Pro Arg Ser
1               5                   10

<210> SEQ ID NO 56
<211> LENGTH: 12
<212> TYPE: PRT
<213> ORGANISM: Artificial Sequence
<220> FEATURE:
<223> OTHER INFORMATION: Synthetic Peptide 1-24

<400> SEQUENCE: 56

Arg Asn Pro Gly Asn Gly Pro Gly Thr Pro Arg Ser
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Synthetic Peptide 1-25

<400> SEQUENCE: 57

Arg Asn Pro Gly Thr Gly Pro Gly Asn Pro Arg Ser
1               5                   10

<210> SEQ ID NO 58
<211> LENGTH: 12
<212> TYPE: PRT
<213> ORGANISM: Artificial Sequence
<220> FEATURE:
<223> OTHER INFORMATION: Synthetic Peptide 1-26

<400> SEQUENCE: 58

Arg Asn Pro Gly Thr Gly Pro Gly Thr Pro Arg Ser
1               5                   10

<210> SEQ ID NO 59
<211> LENGTH: 12
<212> TYPE: PRT
<213> ORGANISM: Artificial Sequence
<220> FEATURE:
<223> OTHER INFORMATION: Synthetic Peptide 1-27

<400> SEQUENCE: 59

Arg Asn Pro Gly Asn Gly Pro Gly Leu Pro Arg Ser
1               5                   10

<210> SEQ ID NO 60
```

```
<211> LENGTH: 12
<212> TYPE: PRT
<213> ORGANISM: Artificial Sequence
<220> FEATURE:
<223> OTHER INFORMATION: Synthetic Peptide 1-28

<400> SEQUENCE: 60

Arg Asn Pro Gly Leu Gly Pro Gly Asn Pro Arg Ser
1               5                   10

<210> SEQ ID NO 61
<211> LENGTH: 12
<212> TYPE: PRT
<213> ORGANISM: Artificial Sequence
<220> FEATURE:
<223> OTHER INFORMATION: Synthetic Peptide 1-29

<400> SEQUENCE: 61

Arg Asn Pro Gly Leu Gly Pro Gly Leu Pro Arg Ser
1               5                   10

<210> SEQ ID NO 62
<211> LENGTH: 12
<212> TYPE: PRT
<213> ORGANISM: Artificial Sequence
<220> FEATURE:
<223> OTHER INFORMATION: Synthetic Peptide 1-30

<400> SEQUENCE: 62

Arg Met Pro Gly Met Gly Pro Gly Gln Pro Arg Ser
1               5                   10

<210> SEQ ID NO 63
<211> LENGTH: 12
<212> TYPE: PRT
<213> ORGANISM: Artificial Sequence
<220> FEATURE:
<223> OTHER INFORMATION: Synthetic Peptide 1-31

<400> SEQUENCE: 63

Arg Met Pro Gly Gln Gly Pro Gly Met Pro Arg Ser
1               5                   10

<210> SEQ ID NO 64
<211> LENGTH: 12
<212> TYPE: PRT
<213> ORGANISM: Artificial Sequence
<220> FEATURE:
<223> OTHER INFORMATION: Synthetic Peptide 1-32

<400> SEQUENCE: 64

Arg Met Pro Gly Gln Gly Pro Gly Gln Pro Arg Ser
1               5                   10

<210> SEQ ID NO 65
<211> LENGTH: 12
<212> TYPE: PRT
<213> ORGANISM: Artificial Sequence
<220> FEATURE:
<223> OTHER INFORMATION: Synthetic Peptide 1-33

<400> SEQUENCE: 65

Arg Met Pro Gly Met Gly Pro Gly Asn Pro Arg Ser
1               5                   10

<210> SEQ ID NO 66
<211> LENGTH: 12
```

```
<212> TYPE: PRT
<213> ORGANISM: Artificial Sequence
<220> FEATURE:
<223> OTHER INFORMATION: Synthetic Peptide 1-34

<400> SEQUENCE: 66

Arg Met Pro Gly Asn Gly Pro Gly Met Pro Arg Ser
1               5                   10

<210> SEQ ID NO 67
<211> LENGTH: 12
<212> TYPE: PRT
<213> ORGANISM: Artificial Sequence
<220> FEATURE:
<223> OTHER INFORMATION: Synthetic Peptide 1-35

<400> SEQUENCE: 67

Arg Met Pro Gly Asn Gly Pro Gly Asn Pro Arg Ser
1               5                   10

<210> SEQ ID NO 68
<211> LENGTH: 12
<212> TYPE: PRT
<213> ORGANISM: Artificial Sequence
<220> FEATURE:
<223> OTHER INFORMATION: Synthetic Peptide 1-36

<400> SEQUENCE: 68

Arg Met Pro Gly Met Gly Pro Gly Thr Pro Arg Ser
1               5                   10

<210> SEQ ID NO 69
<211> LENGTH: 12
<212> TYPE: PRT
<213> ORGANISM: Artificial Sequence
<220> FEATURE:
<223> OTHER INFORMATION: Synthetic Peptide 1-37

<400> SEQUENCE: 69

Arg Met Pro Gly Thr Gly Pro Gly Met Pro Arg Ser
1               5                   10

<210> SEQ ID NO 70
<211> LENGTH: 12
<212> TYPE: PRT
<213> ORGANISM: Artificial Sequence
<220> FEATURE:
<223> OTHER INFORMATION: Synthetic Peptide 1-38

<400> SEQUENCE: 70

Arg Met Pro Gly Thr Gly Pro Gly Thr Pro Arg Ser
1               5                   10

<210> SEQ ID NO 71
<211> LENGTH: 12
<212> TYPE: PRT
<213> ORGANISM: Artificial Sequence
<220> FEATURE:
<223> OTHER INFORMATION: Synthetic Peptide 1-39

<400> SEQUENCE: 71

Arg Met Pro Gly Met Gly Pro Gly Leu Pro Arg Ser
1               5                   10

<210> SEQ ID NO 72
<211> LENGTH: 12
<212> TYPE: PRT
```

<213> ORGANISM: Artificial Sequence
<220> FEATURE:
<223> OTHER INFORMATION: Synthetic Peptide 1-40

<400> SEQUENCE: 72

Arg Met Gly Leu Gly Pro Gly Met Pro Arg Ser
1               5                   10

<210> SEQ ID NO 73
<211> LENGTH: 12
<212> TYPE: PRT
<213> ORGANISM: Artificial Sequence
<220> FEATURE:
<223> OTHER INFORMATION: Synthetic Peptide 1-41

<400> SEQUENCE: 73

Arg Met Pro Gly Leu Gly Pro Gly Leu Pro Arg Ser
1               5                   10

<210> SEQ ID NO 74
<211> LENGTH: 12
<212> TYPE: PRT
<213> ORGANISM: Artificial Sequence
<220> FEATURE:
<223> OTHER INFORMATION: Synthetic Peptide 1-42

<400> SEQUENCE: 74

Arg Thr Pro Gly Thr Gly Pro Gly Gln Pro Arg Ser
1               5                   10

<210> SEQ ID NO 75
<211> LENGTH: 12
<212> TYPE: PRT
<213> ORGANISM: Artificial Sequence
<220> FEATURE:
<223> OTHER INFORMATION: Synthetic Peptide 1-43

<400> SEQUENCE: 75

Arg Thr Pro Gly Gln Gly Pro Gly Thr Pro Arg Ser
1               5                   10

<210> SEQ ID NO 76
<211> LENGTH: 12
<212> TYPE: PRT
<213> ORGANISM: Artificial Sequence
<220> FEATURE:
<223> OTHER INFORMATION: Synthetic Peptide 1-44

<400> SEQUENCE: 76

Arg Thr Pro Gly Gln Gly Pro Gly Gln Pro Arg Ser
1               5                   10

<210> SEQ ID NO 77
<211> LENGTH: 12
<212> TYPE: PRT
<213> ORGANISM: Artificial Sequence
<220> FEATURE:
<223> OTHER INFORMATION: Synthetic Peptide 1-45

<400> SEQUENCE: 77

Arg Thr Pro Gly Thr Gly Pro Gly Asn Pro Arg Ser
1               5                   10

<210> SEQ ID NO 78
<211> LENGTH: 12
<212> TYPE: PRT
<213> ORGANISM: Artificial Sequence
<220> FEATURE:
<223> OTHER INFORMATION: Synthetic Peptide 1-46

<400> SEQUENCE: 78

Arg Thr Pro Gly Asn Gly Pro Gly Thr Pro Arg Ser
1               5                   10

<210> SEQ ID NO 79
<211> LENGTH: 12
<212> TYPE: PRT
<213> ORGANISM: Artificial Sequence
<220> FEATURE:
<223> OTHER INFORMATION: Synthetic Peptide 1-47

<400> SEQUENCE: 79

Arg Thr Pro Gly Asn Gly Pro Gly Asn Pro Arg Ser
1               5                   10

<210> SEQ ID NO 80
<211> LENGTH: 12
<212> TYPE: PRT
<213> ORGANISM: Artificial Sequence
<220> FEATURE:
<223> OTHER INFORMATION: Synthetic Peptide 1-48

<400> SEQUENCE: 80

Arg Thr Pro Gly Thr Gly Pro Gly Met Pro Arg Ser
1               5                   10

<210> SEQ ID NO 81
<211> LENGTH: 12
<212> TYPE: PRT
<213> ORGANISM: Artificial Sequence
<220> FEATURE:
<223> OTHER INFORMATION: Synthetic Peptide 1-49

<400> SEQUENCE: 81

Arg Thr Pro Gly Met Gly Pro Gly Thr Pro Arg Ser
1               5                   10

<210> SEQ ID NO 82
<211> LENGTH: 12
<212> TYPE: PRT
<213> ORGANISM: Artificial Sequence
<220> FEATURE:
<223> OTHER INFORMATION: Synthetic Peptide 1-50

<400> SEQUENCE: 82

Arg Thr Pro Gly Met Gly Pro Gly Met Pro Arg Ser
1               5                   10

<210> SEQ ID NO 83
<211> LENGTH: 12
<212> TYPE: PRT
<213> ORGANISM: Artificial Sequence
<220> FEATURE:
<223> OTHER INFORMATION: Synthetic Peptide 1-51

<400> SEQUENCE: 83

Arg Thr Pro Gly Thr Gly Pro Gly Leu Pro Arg Ser
1               5                   10

<210> SEQ ID NO 84
<211> LENGTH: 12
<212> TYPE: PRT
<213> ORGANISM: Artificial Sequence
<220> FEATURE:

<223> OTHER INFORMATION: Synthetic Peptide 1-52

<400> SEQUENCE: 84

Arg Thr Pro Gly Leu Gly Pro Gly Thr Pro Arg Ser
1               5                   10

<210> SEQ ID NO 85
<211> LENGTH: 12
<212> TYPE: PRT
<213> ORGANISM: Artificial Sequence
<220> FEATURE:
<223> OTHER INFORMATION: Synthetic Peptide 1-53

<400> SEQUENCE: 85

Arg Thr Pro Gly Leu Gly Pro Gly Leu Pro Arg Ser
1               5                   10

<210> SEQ ID NO 86
<211> LENGTH: 12
<212> TYPE: PRT
<213> ORGANISM: Artificial Sequence
<220> FEATURE:
<223> OTHER INFORMATION: Synthetic Peptide 1-54

<400> SEQUENCE: 86

Arg Leu Pro Gly Leu Gly Pro Gly Gln Pro Arg Ser
1               5                   10

<210> SEQ ID NO 87
<211> LENGTH: 12
<212> TYPE: PRT
<213> ORGANISM: Artificial Sequence
<220> FEATURE:
<223> OTHER INFORMATION: Synthetic Peptide 1-55

<400> SEQUENCE: 87

Arg Leu Pro Gly Gln Gly Pro Gly Leu Pro Arg Ser
1               5                   10

<210> SEQ ID NO 88
<211> LENGTH: 12
<212> TYPE: PRT
<213> ORGANISM: Artificial Sequence
<220> FEATURE:
<223> OTHER INFORMATION: Synthetic Peptide 1-56

<400> SEQUENCE: 88

Arg Leu Pro Gly Gln Gly Pro Gly Gln Pro Arg Ser
1               5                   10

<210> SEQ ID NO 89
<211> LENGTH: 12
<212> TYPE: PRT
<213> ORGANISM: Artificial Sequence
<220> FEATURE:
<223> OTHER INFORMATION: Synthetic Peptide 1-57

<400> SEQUENCE: 89

Arg Leu Pro Gly Leu Gly Pro Gly Asn Pro Arg Ser
1               5                   10

<210> SEQ ID NO 90
<211> LENGTH: 12
<212> TYPE: PRT
<213> ORGANISM: Artificial Sequence
<220> FEATURE:
<223> OTHER INFORMATION: Synthetic Peptide 1-58

<400> SEQUENCE: 90

Arg Leu Pro Gly Asn Gly Pro Gly Leu Pro Arg Ser
1               5                   10

<210> SEQ ID NO 91
<211> LENGTH: 12
<212> TYPE: PRT
<213> ORGANISM: Artificial Sequence
<220> FEATURE:
<223> OTHER INFORMATION: Synthetic Peptide 1-59

<400> SEQUENCE: 91

Arg Leu Pro Gly Asn Gly Pro Gly Asn Pro Arg Ser
1               5                   10

<210> SEQ ID NO 92
<211> LENGTH: 12
<212> TYPE: PRT
<213> ORGANISM: Artificial Sequence
<220> FEATURE:
<223> OTHER INFORMATION: Synthetic Peptide 1-60

<400> SEQUENCE: 92

Arg Leu Pro Gly Leu Gly Pro Gly Met Pro Arg Ser
1               5                   10

<210> SEQ ID NO 93
<211> LENGTH: 12
<212> TYPE: PRT
<213> ORGANISM: Artificial Sequence
<220> FEATURE:
<223> OTHER INFORMATION: Synthetic Peptide 1-61

<400> SEQUENCE: 93

Arg Leu Pro Gly Met Gly Pro Gly Leu Pro Arg Ser
1               5                   10

<210> SEQ ID NO 94
<211> LENGTH: 12
<212> TYPE: PRT
<213> ORGANISM: Artificial Sequence
<220> FEATURE:
<223> OTHER INFORMATION: Synthetic Peptide 1-62

<400> SEQUENCE: 94

Arg Leu Pro Gly Met Gly Pro Gly Met Pro Arg Ser
1               5                   10

<210> SEQ ID NO 95
<211> LENGTH: 12
<212> TYPE: PRT
<213> ORGANISM: Artificial Sequence
<220> FEATURE:
<223> OTHER INFORMATION: Synthetic Peptide 1-63

<400> SEQUENCE: 95

Arg Leu Pro Gly Leu Gly Pro Gly Thr Pro Arg Ser
1               5                   10

<210> SEQ ID NO 96
<211> LENGTH: 12
<212> TYPE: PRT
<213> ORGANISM: Artificial Sequence
<220> FEATURE:
<223> OTHER INFORMATION: Synthetic Peptide 1-64

```
<400> SEQUENCE: 96

Arg Leu Pro Gly Thr Gly Pro Gly Leu Pro Arg Ser
1               5                   10

<210> SEQ ID NO 97
<211> LENGTH: 12
<212> TYPE: PRT
<213> ORGANISM: Artificial Sequence
<220> FEATURE:
<223> OTHER INFORMATION: Synthetic Peptide 1-65

<400> SEQUENCE: 97

Arg Leu Pro Gly Thr Gly Pro Gly Thr Pro Arg Ser
1               5                   10

<210> SEQ ID NO 98
<211> LENGTH: 12
<212> TYPE: PRT
<213> ORGANISM: Artificial Sequence
<220> FEATURE:
<223> OTHER INFORMATION: Synthetic Peptide 1-66

<400> SEQUENCE: 98

Arg Gln Pro Gln Gln Gln Pro Gln Gln Pro Arg Ser
1               5                   10

<210> SEQ ID NO 99
<211> LENGTH: 12
<212> TYPE: PRT
<213> ORGANISM: Artificial Sequence
<220> FEATURE:
<223> OTHER INFORMATION: Synthetic Peptide 1-67

<400> SEQUENCE: 99

Arg Asn Pro Asn Asn Asn Pro Asn Asn Pro Arg Ser
1               5                   10

<210> SEQ ID NO 100
<211> LENGTH: 12
<212> TYPE: PRT
<213> ORGANISM: Artificial Sequence
<220> FEATURE:
<223> OTHER INFORMATION: Synthetic Peptide 1-68

<400> SEQUENCE: 100

Arg Met Pro Met Met Met Pro Met Met Pro Arg Ser
1               5                   10

<210> SEQ ID NO 101
<211> LENGTH: 12
<212> TYPE: PRT
<213> ORGANISM: Artificial Sequence
<220> FEATURE:
<223> OTHER INFORMATION: Synthetic Peptide 1-69

<400> SEQUENCE: 101

Arg Thr Pro Thr Thr Thr Pro Thr Thr Pro Arg Ser
1               5                   10

<210> SEQ ID NO 102
<211> LENGTH: 12
<212> TYPE: PRT
<213> ORGANISM: Artificial Sequence
<220> FEATURE:
<223> OTHER INFORMATION: Synthetic Peptide 1-70

<400> SEQUENCE: 102
```

```
Arg Leu Pro Leu Leu Leu Pro Leu Leu Pro Arg Ser
1               5                   10
```

<210> SEQ ID NO 103
<211> LENGTH: 12
<212> TYPE: PRT
<213> ORGANISM: Artificial Sequence
<220> FEATURE:
<223> OTHER INFORMATION: Synthetic Peptide 2-1

<400> SEQUENCE: 103

```
Arg Gln Pro Gly Gln Gly Pro Gly Gln Gly Arg Ser
1               5                   10
```

<210> SEQ ID NO 104
<211> LENGTH: 12
<212> TYPE: PRT
<213> ORGANISM: Artificial Sequence
<220> FEATURE:
<223> OTHER INFORMATION: Synthetic Peptide 2-2

<400> SEQUENCE: 104

```
Arg Asn Pro Gly Asn Gly Pro Gly Asn Gly Arg Ser
1               5                   10
```

<210> SEQ ID NO 105
<211> LENGTH: 12
<212> TYPE: PRT
<213> ORGANISM: Artificial Sequence
<220> FEATURE:
<223> OTHER INFORMATION: Synthetic Peptide 2-3

<400> SEQUENCE: 105

```
Arg Met Pro Gly Met Gly Pro Gly Met Gly Arg Ser
1               5                   10
```

<210> SEQ ID NO 106
<211> LENGTH: 12
<212> TYPE: PRT
<213> ORGANISM: Artificial Sequence
<220> FEATURE:
<223> OTHER INFORMATION: Synthetic Peptide 2-4

<400> SEQUENCE: 106

```
Arg Thr Pro Gly Thr Gly Pro Gly Thr Gly Arg Ser
1               5                   10
```

<210> SEQ ID NO 107
<211> LENGTH: 12
<212> TYPE: PRT
<213> ORGANISM: Artificial Sequence
<220> FEATURE:
<223> OTHER INFORMATION: Synthetic Peptide 2-5

<400> SEQUENCE: 107

```
Arg Leu Pro Gly Leu Gly Pro Gly Leu Gly Arg Ser
1               5                   10
```

<210> SEQ ID NO 108
<211> LENGTH: 12
<212> TYPE: PRT
<213> ORGANISM: Artificial Sequence
<220> FEATURE:
<223> OTHER INFORMATION: Synthetic Peptide 2-6

<400> SEQUENCE: 108

Arg Gln Pro Gly Gln Gly Pro Gly Asn Gly Arg Ser
1               5                   10

<210> SEQ ID NO 109
<211> LENGTH: 12
<212> TYPE: PRT
<213> ORGANISM: Artificial Sequence
<220> FEATURE:
<223> OTHER INFORMATION: Synthetic Peptide 2-7

<400> SEQUENCE: 109

Arg Gln Pro Gly Asn Gly Pro Gly Gln Gly Arg Ser
1               5                   10

<210> SEQ ID NO 110
<211> LENGTH: 12
<212> TYPE: PRT
<213> ORGANISM: Artificial Sequence
<220> FEATURE:
<223> OTHER INFORMATION: Synthetic Peptide 2-8

<400> SEQUENCE: 110

Arg Gln Pro Gly Asn Gly Pro Gly Asn Gly Arg Ser
1               5                   10

<210> SEQ ID NO 111
<211> LENGTH: 12
<212> TYPE: PRT
<213> ORGANISM: Artificial Sequence
<220> FEATURE:
<223> OTHER INFORMATION: Synthetic Peptide 2-9

<400> SEQUENCE: 111

Arg Gln Pro Gly Gln Gly Pro Gly Met Gly Arg Ser
1               5                   10

<210> SEQ ID NO 112
<211> LENGTH: 12
<212> TYPE: PRT
<213> ORGANISM: Artificial Sequence
<220> FEATURE:
<223> OTHER INFORMATION: Synthetic Peptide 2-10

<400> SEQUENCE: 112

Arg Gln Pro Gly Met Gly Pro Gly Gln Gly Arg Ser
1               5                   10

<210> SEQ ID NO 113
<211> LENGTH: 12
<212> TYPE: PRT
<213> ORGANISM: Artificial Sequence
<220> FEATURE:
<223> OTHER INFORMATION: Synthetic Peptide 2-11

<400> SEQUENCE: 113

Arg Gln Pro Gly Met Gly Pro Gly Met Gly Arg Ser
1               5                   10

<210> SEQ ID NO 114
<211> LENGTH: 12
<212> TYPE: PRT
<213> ORGANISM: Artificial Sequence
<220> FEATURE:
<223> OTHER INFORMATION: Synthetic Peptide 2-12

<400> SEQUENCE: 114

Arg Gln Pro Gly Gln Gly Pro Gly Thr Gly Arg Ser

```
1               5                   10
```

<210> SEQ ID NO 115
<211> LENGTH: 12
<212> TYPE: PRT
<213> ORGANISM: Artificial Sequence
<220> FEATURE:
<223> OTHER INFORMATION: Synthetic Peptide 2-13

<400> SEQUENCE: 115

```
Arg Gln Pro Gly Thr Gly Pro Gly Gln Gly Arg Ser
1               5                   10
```

<210> SEQ ID NO 116
<211> LENGTH: 12
<212> TYPE: PRT
<213> ORGANISM: Artificial Sequence
<220> FEATURE:
<223> OTHER INFORMATION: Synthetic Peptide 2-14

<400> SEQUENCE: 116

```
Arg Gln Pro Gly Thr Gly Pro Gly Thr Gly Arg Ser
1               5                   10
```

<210> SEQ ID NO 117
<211> LENGTH: 12
<212> TYPE: PRT
<213> ORGANISM: Artificial Sequence
<220> FEATURE:
<223> OTHER INFORMATION: Synthetic Peptide 2-15

<400> SEQUENCE: 117

```
Arg Gln Pro Gly Gln Gly Pro Gly Leu Gly Arg Ser
1               5                   10
```

<210> SEQ ID NO 118
<211> LENGTH: 12
<212> TYPE: PRT
<213> ORGANISM: Artificial Sequence
<220> FEATURE:
<223> OTHER INFORMATION: Synthetic Peptide 2-16

<400> SEQUENCE: 118

```
Arg Gln Pro Gly Leu Gly Pro Gly Gln Gly Arg Ser
1               5                   10
```

<210> SEQ ID NO 119
<211> LENGTH: 12
<212> TYPE: PRT
<213> ORGANISM: Artificial Sequence
<220> FEATURE:
<223> OTHER INFORMATION: Synthetic Peptide 2-17

<400> SEQUENCE: 119

```
Arg Gln Pro Gly Leu Gly Pro Gly Leu Gly Arg Ser
1               5                   10
```

<210> SEQ ID NO 120
<211> LENGTH: 12
<212> TYPE: PRT
<213> ORGANISM: Artificial Sequence
<220> FEATURE:
<223> OTHER INFORMATION: Synthetic Peptide 2-18

<400> SEQUENCE: 120

```
Arg Asn Pro Gly Asn Gly Pro Gly Gln Gly Arg Ser
1               5                   10
```

```
<210> SEQ ID NO 121
<211> LENGTH: 12
<212> TYPE: PRT
<213> ORGANISM: Artificial Sequence
<220> FEATURE:
<223> OTHER INFORMATION: Synthetic Peptide 2-19

<400> SEQUENCE: 121

Arg Asn Pro Gly Gln Gly Pro Gly Asn Gly Arg Ser
1               5                   10

<210> SEQ ID NO 122
<211> LENGTH: 12
<212> TYPE: PRT
<213> ORGANISM: Artificial Sequence
<220> FEATURE:
<223> OTHER INFORMATION: Synthetic Peptide 2-20

<400> SEQUENCE: 122

Arg Asn Pro Gly Gln Gly Pro Gly Gln Gly Arg Ser
1               5                   10

<210> SEQ ID NO 123
<211> LENGTH: 12
<212> TYPE: PRT
<213> ORGANISM: Artificial Sequence
<220> FEATURE:
<223> OTHER INFORMATION: Synthetic Peptide 2-21

<400> SEQUENCE: 123

Arg Asn Pro Gly Asn Gly Pro Gly Met Gly Arg Ser
1               5                   10

<210> SEQ ID NO 124
<211> LENGTH: 12
<212> TYPE: PRT
<213> ORGANISM: Artificial Sequence
<220> FEATURE:
<223> OTHER INFORMATION: Synthetic Peptide 2-22

<400> SEQUENCE: 124

Arg Asn Pro Gly Met Gly Pro Gly Asn Gly Arg Ser
1               5                   10

<210> SEQ ID NO 125
<211> LENGTH: 12
<212> TYPE: PRT
<213> ORGANISM: Artificial Sequence
<220> FEATURE:
<223> OTHER INFORMATION: Synthetic Peptide 2-23

<400> SEQUENCE: 125

Arg Asn Pro Gly Met Gly Pro Gly Met Gly Arg Ser
1               5                   10

<210> SEQ ID NO 126
<211> LENGTH: 12
<212> TYPE: PRT
<213> ORGANISM: Artificial Sequence
<220> FEATURE:
<223> OTHER INFORMATION: Synthetic Peptide 2-24

<400> SEQUENCE: 126

Arg Asn Pro Gly Asn Gly Pro Gly Thr Gly Arg Ser
1               5                   10
```

<210> SEQ ID NO 127
<211> LENGTH: 12
<212> TYPE: PRT
<213> ORGANISM: Artificial Sequence
<220> FEATURE:
<223> OTHER INFORMATION: Synthetic Peptide 2-25

<400> SEQUENCE: 127

Arg Asn Pro Gly Thr Gly Pro Gly Asn Gly Arg Ser
1               5                   10

<210> SEQ ID NO 128
<211> LENGTH: 12
<212> TYPE: PRT
<213> ORGANISM: Artificial Sequence
<220> FEATURE:
<223> OTHER INFORMATION: Synthetic Peptide 2-26

<400> SEQUENCE: 128

Arg Asn Pro Gly Thr Gly Pro Gly Thr Gly Arg Ser
1               5                   10

<210> SEQ ID NO 129
<211> LENGTH: 12
<212> TYPE: PRT
<213> ORGANISM: Artificial Sequence
<220> FEATURE:
<223> OTHER INFORMATION: Synthetic Peptide 2-27

<400> SEQUENCE: 129

Arg Asn Pro Gly Asn Gly Pro Gly Leu Gly Arg Ser
1               5                   10

<210> SEQ ID NO 130
<211> LENGTH: 12
<212> TYPE: PRT
<213> ORGANISM: Artificial Sequence
<220> FEATURE:
<223> OTHER INFORMATION: Synthetic Peptide 2-28

<400> SEQUENCE: 130

Arg Asn Pro Gly Leu Gly Pro Gly Asn Gly Arg Ser
1               5                   10

<210> SEQ ID NO 131
<211> LENGTH: 12
<212> TYPE: PRT
<213> ORGANISM: Artificial Sequence
<220> FEATURE:
<223> OTHER INFORMATION: Synthetic Peptide 2-29

<400> SEQUENCE: 131

Arg Asn Pro Gly Leu Gly Pro Gly Leu Gly Arg Ser
1               5                   10

<210> SEQ ID NO 132
<211> LENGTH: 12
<212> TYPE: PRT
<213> ORGANISM: Artificial Sequence
<220> FEATURE:
<223> OTHER INFORMATION: Synthetic Peptide 2-30

<400> SEQUENCE: 132

Arg Met Pro Gly Met Gly Pro Gly Gln Gly Arg Ser
1               5                   10

```
<210> SEQ ID NO 133
<211> LENGTH: 12
<212> TYPE: PRT
<213> ORGANISM: Artificial Sequence
<220> FEATURE:
<223> OTHER INFORMATION: Synthetic Peptide 2-31

<400> SEQUENCE: 133

Arg Met Pro Gly Gln Gly Pro Gly Met Gly Arg Ser
1               5                   10

<210> SEQ ID NO 134
<211> LENGTH: 12
<212> TYPE: PRT
<213> ORGANISM: Artificial Sequence
<220> FEATURE:
<223> OTHER INFORMATION: Synthetic Peptide 2-32

<400> SEQUENCE: 134

Arg Met Pro Gly Gln Gly Pro Gly Gln Gly Arg Ser
1               5                   10

<210> SEQ ID NO 135
<211> LENGTH: 12
<212> TYPE: PRT
<213> ORGANISM: Artificial Sequence
<220> FEATURE:
<223> OTHER INFORMATION: Synthetic Peptide 2-33

<400> SEQUENCE: 135

Arg Met Pro Gly Met Gly Pro Gly Asn Gly Arg Ser
1               5                   10

<210> SEQ ID NO 136
<211> LENGTH: 12
<212> TYPE: PRT
<213> ORGANISM: Artificial Sequence
<220> FEATURE:
<223> OTHER INFORMATION: Synthetic Peptide 2-34

<400> SEQUENCE: 136

Arg Met Pro Gly Asn Gly Pro Gly Met Gly Arg Ser
1               5                   10

<210> SEQ ID NO 137
<211> LENGTH: 12
<212> TYPE: PRT
<213> ORGANISM: Artificial Sequence
<220> FEATURE:
<223> OTHER INFORMATION: Synthetic Peptide 2-35

<400> SEQUENCE: 137

Arg Met Pro Gly Asn Gly Pro Gly Asn Gly Arg Ser
1               5                   10

<210> SEQ ID NO 138
<211> LENGTH: 12
<212> TYPE: PRT
<213> ORGANISM: Artificial Sequence
<220> FEATURE:
<223> OTHER INFORMATION: Synthetic Peptide 2-36

<400> SEQUENCE: 138

Arg Met Pro Gly Met Gly Pro Gly Thr Gly Arg Ser
1               5                   10

<210> SEQ ID NO 139
```

```
<211> LENGTH: 12
<212> TYPE: PRT
<213> ORGANISM: Artificial Sequence
<220> FEATURE:
<223> OTHER INFORMATION: Synthetic Peptide 2-37

<400> SEQUENCE: 139

Arg Met Pro Gly Thr Gly Pro Gly Met Gly Arg Ser
1               5                   10

<210> SEQ ID NO 140
<211> LENGTH: 12
<212> TYPE: PRT
<213> ORGANISM: Artificial Sequence
<220> FEATURE:
<223> OTHER INFORMATION: Synthetic Peptide 2-38

<400> SEQUENCE: 140

Arg Met Pro Gly Thr Gly Pro Gly Thr Gly Arg Ser
1               5                   10

<210> SEQ ID NO 141
<211> LENGTH: 12
<212> TYPE: PRT
<213> ORGANISM: Artificial Sequence
<220> FEATURE:
<223> OTHER INFORMATION: Synthetic Peptide 2-39

<400> SEQUENCE: 141

Arg Met Pro Gly Met Gly Pro Gly Leu Gly Arg Ser
1               5                   10

<210> SEQ ID NO 142
<211> LENGTH: 12
<212> TYPE: PRT
<213> ORGANISM: Artificial Sequence
<220> FEATURE:
<223> OTHER INFORMATION: Synthetic Peptide 2-40

<400> SEQUENCE: 142

Arg Met Pro Gly Leu Gly Pro Gly Met Gly Arg Ser
1               5                   10

<210> SEQ ID NO 143
<211> LENGTH: 12
<212> TYPE: PRT
<213> ORGANISM: Artificial Sequence
<220> FEATURE:
<223> OTHER INFORMATION: Synthetic Peptide 2-41

<400> SEQUENCE: 143

Arg Met Pro Gly Leu Gly Pro Gly Leu Gly Arg Ser
1               5                   10

<210> SEQ ID NO 144
<211> LENGTH: 12
<212> TYPE: PRT
<213> ORGANISM: Artificial Sequence
<220> FEATURE:
<223> OTHER INFORMATION: Synthetic Peptide 2-42

<400> SEQUENCE: 144

Arg Thr Pro Gly Thr Gly Pro Gly Gln Gly Arg Ser
1               5                   10

<210> SEQ ID NO 145
<211> LENGTH: 12
```

```
<212> TYPE: PRT
<213> ORGANISM: Artificial Sequence
<220> FEATURE:
<223> OTHER INFORMATION: Synthetic Peptide 2-43

<400> SEQUENCE: 145

Arg Thr Pro Gly Gln Gly Pro Gly Thr Gly Arg Ser
1               5                   10

<210> SEQ ID NO 146
<211> LENGTH: 12
<212> TYPE: PRT
<213> ORGANISM: Artificial Sequence
<220> FEATURE:
<223> OTHER INFORMATION: Synthetic Peptide 2-44

<400> SEQUENCE: 146

Arg Thr Pro Gly Gln Gly Pro Gly Gln Gly Arg Ser
1               5                   10

<210> SEQ ID NO 147
<211> LENGTH: 12
<212> TYPE: PRT
<213> ORGANISM: Artificial Sequence
<220> FEATURE:
<223> OTHER INFORMATION: Synthetic Peptide 2-45

<400> SEQUENCE: 147

Arg Thr Pro Gly Thr Gly Pro Gly Asn Gly Arg Ser
1               5                   10

<210> SEQ ID NO 148
<211> LENGTH: 12
<212> TYPE: PRT
<213> ORGANISM: Artificial Sequence
<220> FEATURE:
<223> OTHER INFORMATION: Synthetic Peptide 2-46

<400> SEQUENCE: 148

Arg Thr Pro Gly Asn Gly Pro Gly Thr Gly Arg Ser
1               5                   10

<210> SEQ ID NO 149
<211> LENGTH: 12
<212> TYPE: PRT
<213> ORGANISM: Artificial Sequence
<220> FEATURE:
<223> OTHER INFORMATION: Synthetic Peptide 2-47

<400> SEQUENCE: 149

Arg Thr Pro Gly Asn Gly Pro Gly Asn Gly Arg Ser
1               5                   10

<210> SEQ ID NO 150
<211> LENGTH: 12
<212> TYPE: PRT
<213> ORGANISM: Artificial Sequence
<220> FEATURE:
<223> OTHER INFORMATION: Synthetic Peptide 2-48

<400> SEQUENCE: 150

Arg Thr Pro Gly Thr Gly Pro Gly Met Gly Arg Ser
1               5                   10

<210> SEQ ID NO 151
<211> LENGTH: 12
<212> TYPE: PRT
```

<213> ORGANISM: Artificial Sequence
<220> FEATURE:
<223> OTHER INFORMATION: Synthetic Peptide 2-49

<400> SEQUENCE: 151

Arg Thr Pro Gly Met Gly Pro Gly Thr Gly Arg Ser
1               5                   10

<210> SEQ ID NO 152
<211> LENGTH: 12
<212> TYPE: PRT
<213> ORGANISM: Artificial Sequence
<220> FEATURE:
<223> OTHER INFORMATION: Synthetic Peptide 2-50

<400> SEQUENCE: 152

Arg Thr Pro Gly Met Gly Pro Gly Met Gly Arg Ser
1               5                   10

<210> SEQ ID NO 153
<211> LENGTH: 12
<212> TYPE: PRT
<213> ORGANISM: Artificial Sequence
<220> FEATURE:
<223> OTHER INFORMATION: Synthetic Peptide 2-51

<400> SEQUENCE: 153

Arg Thr Pro Gly Thr Gly Pro Gly Leu Gly Arg Ser
1               5                   10

<210> SEQ ID NO 154
<211> LENGTH: 12
<212> TYPE: PRT
<213> ORGANISM: Artificial Sequence
<220> FEATURE:
<223> OTHER INFORMATION: Synthetic Peptide 2-52

<400> SEQUENCE: 154

Arg Thr Pro Gly Leu Gly Pro Gly Thr Gly Arg Ser
1               5                   10

<210> SEQ ID NO 155
<211> LENGTH: 12
<212> TYPE: PRT
<213> ORGANISM: Artificial Sequence
<220> FEATURE:
<223> OTHER INFORMATION: Synthetic Peptide 2-53

<400> SEQUENCE: 155

Arg Thr Pro Gly Leu Gly Pro Gly Leu Gly Arg Ser
1               5                   10

<210> SEQ ID NO 156
<211> LENGTH: 12
<212> TYPE: PRT
<213> ORGANISM: Artificial Sequence
<220> FEATURE:
<223> OTHER INFORMATION: Synthetic Peptide 2-54

<400> SEQUENCE: 156

Arg Leu Pro Gly Leu Gly Pro Gly Gln Gly Arg Ser
1               5                   10

<210> SEQ ID NO 157
<211> LENGTH: 12
<212> TYPE: PRT
<213> ORGANISM: Artificial Sequence
<220> FEATURE:
<223> OTHER INFORMATION: Synthetic Peptide 2-55

<400> SEQUENCE: 157

Arg Leu Pro Gly Gln Gly Pro Gly Leu Gly Arg Ser
1               5                   10

<210> SEQ ID NO 158
<211> LENGTH: 12
<212> TYPE: PRT
<213> ORGANISM: Artificial Sequence
<220> FEATURE:
<223> OTHER INFORMATION: Synthetic Peptide 2-56

<400> SEQUENCE: 158

Arg Leu Pro Gly Gln Gly Pro Gly Gln Gly Arg Ser
1               5                   10

<210> SEQ ID NO 159
<211> LENGTH: 12
<212> TYPE: PRT
<213> ORGANISM: Artificial Sequence
<220> FEATURE:
<223> OTHER INFORMATION: Synthetic Peptide 2-57

<400> SEQUENCE: 159

Arg Leu Pro Gly Leu Gly Pro Gly Asn Gly Arg Ser
1               5                   10

<210> SEQ ID NO 160
<211> LENGTH: 12
<212> TYPE: PRT
<213> ORGANISM: Artificial Sequence
<220> FEATURE:
<223> OTHER INFORMATION: Synthetic Peptide 2-58

<400> SEQUENCE: 160

Arg Leu Pro Gly Asn Gly Pro Gly Leu Gly Arg Ser
1               5                   10

<210> SEQ ID NO 161
<211> LENGTH: 12
<212> TYPE: PRT
<213> ORGANISM: Artificial Sequence
<220> FEATURE:
<223> OTHER INFORMATION: Synthetic Peptide 2-59

<400> SEQUENCE: 161

Arg Leu Pro Gly Asn Gly Pro Gly Asn Gly Arg Ser
1               5                   10

<210> SEQ ID NO 162
<211> LENGTH: 12
<212> TYPE: PRT
<213> ORGANISM: Artificial Sequence
<220> FEATURE:
<223> OTHER INFORMATION: Synthetic Peptide 2-60

<400> SEQUENCE: 162

Arg Leu Pro Gly Leu Gly Pro Gly Met Gly Arg Ser
1               5                   10

<210> SEQ ID NO 163
<211> LENGTH: 12
<212> TYPE: PRT
<213> ORGANISM: Artificial Sequence
<220> FEATURE:

```
<223> OTHER INFORMATION: Synthetic Peptide 2-61

<400> SEQUENCE: 163

Arg Leu Pro Gly Met Gly Pro Gly Leu Gly Arg Ser
1               5                   10

<210> SEQ ID NO 164
<211> LENGTH: 12
<212> TYPE: PRT
<213> ORGANISM: Artificial Sequence
<220> FEATURE:
<223> OTHER INFORMATION: Synthetic Peptide 2-62

<400> SEQUENCE: 164

Arg Leu Pro Gly Met Gly Pro Gly Met Gly Arg Ser
1               5                   10

<210> SEQ ID NO 165
<211> LENGTH: 12
<212> TYPE: PRT
<213> ORGANISM: Artificial Sequence
<220> FEATURE:
<223> OTHER INFORMATION: Synthetic Peptide 2-63

<400> SEQUENCE: 165

Arg Leu Pro Gly Leu Gly Pro Gly Thr Gly Arg Ser
1               5                   10

<210> SEQ ID NO 166
<211> LENGTH: 12
<212> TYPE: PRT
<213> ORGANISM: Artificial Sequence
<220> FEATURE:
<223> OTHER INFORMATION: Synthetic Peptide 2-64

<400> SEQUENCE: 166

Arg Leu Pro Gly Thr Gly Pro Gly Leu Gly Arg Ser
1               5                   10

<210> SEQ ID NO 167
<211> LENGTH: 12
<212> TYPE: PRT
<213> ORGANISM: Artificial Sequence
<220> FEATURE:
<223> OTHER INFORMATION: Synthetic Peptide 2-65

<400> SEQUENCE: 167

Arg Leu Pro Gly Thr Gly Pro Gly Thr Gly Arg Ser
1               5                   10

<210> SEQ ID NO 168
<211> LENGTH: 12
<212> TYPE: PRT
<213> ORGANISM: Artificial Sequence
<220> FEATURE:
<223> OTHER INFORMATION: Synthetic Peptide 2-66

<400> SEQUENCE: 168

Arg Gln Pro Gln Gln Gln Pro Gln Gln Gly Arg Ser
1               5                   10

<210> SEQ ID NO 169
<211> LENGTH: 12
<212> TYPE: PRT
<213> ORGANISM: Artificial Sequence
<220> FEATURE:
<223> OTHER INFORMATION: Synthetic Peptide 2-67
```

```
<400> SEQUENCE: 169

Arg Asn Pro Asn Asn Pro Asn Asn Gly Arg Ser
1               5                   10

<210> SEQ ID NO 170
<211> LENGTH: 12
<212> TYPE: PRT
<213> ORGANISM: Artificial Sequence
<220> FEATURE:
<223> OTHER INFORMATION: Synthetic Peptide 2-68

<400> SEQUENCE: 170

Arg Met Pro Met Met Pro Met Met Gly Arg Ser
1               5                   10

<210> SEQ ID NO 171
<211> LENGTH: 12
<212> TYPE: PRT
<213> ORGANISM: Artificial Sequence
<220> FEATURE:
<223> OTHER INFORMATION: Synthetic Peptide 2-69

<400> SEQUENCE: 171

Arg Thr Pro Thr Thr Thr Pro Thr Thr Gly Arg Ser
1               5                   10

<210> SEQ ID NO 172
<211> LENGTH: 12
<212> TYPE: PRT
<213> ORGANISM: Artificial Sequence
<220> FEATURE:
<223> OTHER INFORMATION: Synthetic Peptide 2-70

<400> SEQUENCE: 172

Arg Leu Pro Leu Leu Leu Pro Leu Leu Gly Arg Ser
1               5                   10

<210> SEQ ID NO 173
<211> LENGTH: 12
<212> TYPE: PRT
<213> ORGANISM: Artificial Sequence
<220> FEATURE:
<223> OTHER INFORMATION: Synthetic Peptide 3-1

<400> SEQUENCE: 173

Arg Gln Pro Gly Gln Pro Gly Gln Pro Gly Arg Ser
1               5                   10

<210> SEQ ID NO 174
<211> LENGTH: 12
<212> TYPE: PRT
<213> ORGANISM: Artificial Sequence
<220> FEATURE:
<223> OTHER INFORMATION: Synthetic Peptide 3-2

<400> SEQUENCE: 174

Arg Asn Pro Gly Asn Pro Gly Asn Pro Gly Arg Ser
1               5                   10

<210> SEQ ID NO 175
<211> LENGTH: 12
<212> TYPE: PRT
<213> ORGANISM: Artificial Sequence
<220> FEATURE:
<223> OTHER INFORMATION: Synthetic Peptide 3-3
```

```
<400> SEQUENCE: 175

Arg Met Pro Gly Met Pro Gly Met Pro Gly Arg Ser
1               5                   10

<210> SEQ ID NO 176
<211> LENGTH: 12
<212> TYPE: PRT
<213> ORGANISM: Artificial Sequence
<220> FEATURE:
<223> OTHER INFORMATION: Synthetic Peptide 3-4

<400> SEQUENCE: 176

Arg Thr Pro Gly Thr Pro Gly Thr Pro Gly Arg Ser
1               5                   10

<210> SEQ ID NO 177
<211> LENGTH: 12
<212> TYPE: PRT
<213> ORGANISM: Artificial Sequence
<220> FEATURE:
<223> OTHER INFORMATION: Synthetic Peptide 3-5

<400> SEQUENCE: 177

Arg Leu Pro Gly Leu Pro Gly Leu Pro Gly Arg Ser
1               5                   10

<210> SEQ ID NO 178
<211> LENGTH: 12
<212> TYPE: PRT
<213> ORGANISM: Artificial Sequence
<220> FEATURE:
<223> OTHER INFORMATION: Synthetic Peptide 3-6

<400> SEQUENCE: 178

Arg Gln Pro Gly Gln Pro Gly Asn Pro Gly Arg Ser
1               5                   10

<210> SEQ ID NO 179
<211> LENGTH: 12
<212> TYPE: PRT
<213> ORGANISM: Artificial Sequence
<220> FEATURE:
<223> OTHER INFORMATION: Synthetic Peptide 3-7

<400> SEQUENCE: 179

Arg Gln Pro Gly Asn Pro Gly Gln Pro Gly Arg Ser
1               5                   10

<210> SEQ ID NO 180
<211> LENGTH: 12
<212> TYPE: PRT
<213> ORGANISM: Artificial Sequence
<220> FEATURE:
<223> OTHER INFORMATION: Synthetic Peptide 3-8

<400> SEQUENCE: 180

Arg Gln Pro Gly Asn Pro Gly Asn Pro Gly Arg Ser
1               5                   10

<210> SEQ ID NO 181
<211> LENGTH: 12
<212> TYPE: PRT
<213> ORGANISM: Artificial Sequence
<220> FEATURE:
<223> OTHER INFORMATION: Synthetic Peptide 3-9

<400> SEQUENCE: 181
```

Arg Gln Pro Gly Gln Pro Gly Met Pro Gly Arg Ser
1               5                   10

<210> SEQ ID NO 182
<211> LENGTH: 12
<212> TYPE: PRT
<213> ORGANISM: Artificial Sequence
<220> FEATURE:
<223> OTHER INFORMATION: Synthetic Peptide 3-10

<400> SEQUENCE: 182

Arg Gln Pro Gly Met Pro Gly Gln Pro Gly Arg Ser
1               5                   10

<210> SEQ ID NO 183
<211> LENGTH: 12
<212> TYPE: PRT
<213> ORGANISM: Artificial Sequence
<220> FEATURE:
<223> OTHER INFORMATION: Synthetic Peptide 3-11

<400> SEQUENCE: 183

Arg Gln Pro Gly Met Pro Gly Met Pro Gly Arg Ser
1               5                   10

<210> SEQ ID NO 184
<211> LENGTH: 12
<212> TYPE: PRT
<213> ORGANISM: Artificial Sequence
<220> FEATURE:
<223> OTHER INFORMATION: Synthetic Peptide 3-12

<400> SEQUENCE: 184

Arg Gln Pro Gly Gln Pro Gly Thr Pro Gly Arg Ser
1               5                   10

<210> SEQ ID NO 185
<211> LENGTH: 12
<212> TYPE: PRT
<213> ORGANISM: Artificial Sequence
<220> FEATURE:
<223> OTHER INFORMATION: Synthetic Peptide 3-13

<400> SEQUENCE: 185

Arg Gln Pro Gly Thr Pro Gly Gln Pro Gly Arg Ser
1               5                   10

<210> SEQ ID NO 186
<211> LENGTH: 12
<212> TYPE: PRT
<213> ORGANISM: Artificial Sequence
<220> FEATURE:
<223> OTHER INFORMATION: Synthetic Peptide 3-14

<400> SEQUENCE: 186

Arg Gln Pro Gly Thr Pro Gly Thr Pro Gly Arg Ser
1               5                   10

<210> SEQ ID NO 187
<211> LENGTH: 12
<212> TYPE: PRT
<213> ORGANISM: Artificial Sequence
<220> FEATURE:
<223> OTHER INFORMATION: Synthetic Peptide 3-15

<400> SEQUENCE: 187

Arg Gln Pro Gly Gln Pro Gly Leu Pro Gly Arg Ser
1               5                   10

<210> SEQ ID NO 188
<211> LENGTH: 12
<212> TYPE: PRT
<213> ORGANISM: Artificial Sequence
<220> FEATURE:
<223> OTHER INFORMATION: Synthetic Peptide 3-16

<400> SEQUENCE: 188

Arg Gln Pro Gly Leu Pro Gly Gln Pro Gly Arg Ser
1               5                   10

<210> SEQ ID NO 189
<211> LENGTH: 12
<212> TYPE: PRT
<213> ORGANISM: Artificial Sequence
<220> FEATURE:
<223> OTHER INFORMATION: Synthetic Peptide 3-17

<400> SEQUENCE: 189

Arg Gln Pro Gly Leu Pro Gly Leu Pro Gly Arg Ser
1               5                   10

<210> SEQ ID NO 190
<211> LENGTH: 12
<212> TYPE: PRT
<213> ORGANISM: Artificial Sequence
<220> FEATURE:
<223> OTHER INFORMATION: Synthetic Peptide 3-18

<400> SEQUENCE: 190

Arg Asn Pro Gly Asn Pro Gly Gln Pro Gly Arg Ser
1               5                   10

<210> SEQ ID NO 191
<211> LENGTH: 12
<212> TYPE: PRT
<213> ORGANISM: Artificial Sequence
<220> FEATURE:
<223> OTHER INFORMATION: Synthetic Peptide 3-19

<400> SEQUENCE: 191

Arg Asn Pro Gly Gln Pro Gly Asn Pro Gly Arg Ser
1               5                   10

<210> SEQ ID NO 192
<211> LENGTH: 12
<212> TYPE: PRT
<213> ORGANISM: Artificial Sequence
<220> FEATURE:
<223> OTHER INFORMATION: Synthetic Peptide 3-20

<400> SEQUENCE: 192

Arg Asn Pro Gly Gln Pro Gly Gln Pro Gly Arg Ser
1               5                   10

<210> SEQ ID NO 193
<211> LENGTH: 12
<212> TYPE: PRT
<213> ORGANISM: Artificial Sequence
<220> FEATURE:
<223> OTHER INFORMATION: Synthetic Peptide 3-21

<400> SEQUENCE: 193

Arg Asn Pro Gly Asn Pro Gly Met Pro Gly Arg Ser

<210> SEQ ID NO 194
<211> LENGTH: 12
<212> TYPE: PRT
<213> ORGANISM: Artificial Sequence
<220> FEATURE:
<223> OTHER INFORMATION: Synthetic Peptide 3-22

<400> SEQUENCE: 194

Arg Asn Pro Gly Met Pro Gly Asn Pro Gly Arg Ser
1               5                   10

<210> SEQ ID NO 195
<211> LENGTH: 12
<212> TYPE: PRT
<213> ORGANISM: Artificial Sequence
<220> FEATURE:
<223> OTHER INFORMATION: Synthetic Peptide 3-23

<400> SEQUENCE: 195

Arg Asn Pro Gly Met Pro Gly Met Pro Gly Arg Ser
1               5                   10

<210> SEQ ID NO 196
<211> LENGTH: 12
<212> TYPE: PRT
<213> ORGANISM: Artificial Sequence
<220> FEATURE:
<223> OTHER INFORMATION: Synthetic Peptide 3-24

<400> SEQUENCE: 196

Arg Asn Pro Gly Asn Pro Gly Thr Pro Gly Arg Ser
1               5                   10

<210> SEQ ID NO 197
<211> LENGTH: 12
<212> TYPE: PRT
<213> ORGANISM: Artificial Sequence
<220> FEATURE:
<223> OTHER INFORMATION: Synthetic Peptide 3-25

<400> SEQUENCE: 197

Arg Asn Pro Gly Thr Pro Gly Asn Pro Gly Arg Ser
1               5                   10

<210> SEQ ID NO 198
<211> LENGTH: 12
<212> TYPE: PRT
<213> ORGANISM: Artificial Sequence
<220> FEATURE:
<223> OTHER INFORMATION: Synthetic Peptide 3-26

<400> SEQUENCE: 198

Arg Asn Pro Gly Thr Pro Gly Thr Pro Gly Arg Ser
1               5                   10

<210> SEQ ID NO 199
<211> LENGTH: 12
<212> TYPE: PRT
<213> ORGANISM: Artificial Sequence
<220> FEATURE:
<223> OTHER INFORMATION: Synthetic Peptide 3-27

<400> SEQUENCE: 199

Arg Asn Pro Gly Asn Pro Gly Leu Pro Gly Arg Ser
1               5                   10

```
<210> SEQ ID NO 200
<211> LENGTH: 12
<212> TYPE: PRT
<213> ORGANISM: Artificial Sequence
<220> FEATURE:
<223> OTHER INFORMATION: Synthetic Peptide 3-28

<400> SEQUENCE: 200

Arg Asn Pro Gly Leu Pro Gly Asn Pro Gly Arg Ser
1               5                   10

<210> SEQ ID NO 201
<211> LENGTH: 12
<212> TYPE: PRT
<213> ORGANISM: Artificial Sequence
<220> FEATURE:
<223> OTHER INFORMATION: Synthetic Peptide 3-29

<400> SEQUENCE: 201

Arg Asn Pro Gly Leu Pro Gly Leu Pro Gly Arg Ser
1               5                   10

<210> SEQ ID NO 202
<211> LENGTH: 12
<212> TYPE: PRT
<213> ORGANISM: Artificial Sequence
<220> FEATURE:
<223> OTHER INFORMATION: Synthetic Peptide 3-30

<400> SEQUENCE: 202

Arg Met Pro Gly Met Pro Gly Gln Pro Gly Arg Ser
1               5                   10

<210> SEQ ID NO 203
<211> LENGTH: 12
<212> TYPE: PRT
<213> ORGANISM: Artificial Sequence
<220> FEATURE:
<223> OTHER INFORMATION: Synthetic Peptide 3-31

<400> SEQUENCE: 203

Arg Met Pro Gly Gln Pro Gly Met Pro Gly Arg Ser
1               5                   10

<210> SEQ ID NO 204
<211> LENGTH: 12
<212> TYPE: PRT
<213> ORGANISM: Artificial Sequence
<220> FEATURE:
<223> OTHER INFORMATION: Synthetic Peptide 3-32

<400> SEQUENCE: 204

Arg Met Pro Gly Gln Pro Gly Gln Pro Gly Arg Ser
1               5                   10

<210> SEQ ID NO 205
<211> LENGTH: 12
<212> TYPE: PRT
<213> ORGANISM: Artificial Sequence
<220> FEATURE:
<223> OTHER INFORMATION: Synthetic Peptide 3-33

<400> SEQUENCE: 205

Arg Met Pro Gly Met Pro Gly Asn Pro Gly Arg Ser
1               5                   10
```

<210> SEQ ID NO 206
<211> LENGTH: 12
<212> TYPE: PRT
<213> ORGANISM: Artificial Sequence
<220> FEATURE:
<223> OTHER INFORMATION: Synthetic Peptide 3-34

<400> SEQUENCE: 206

Arg Met Pro Gly Asn Pro Gly Met Pro Gly Arg Ser
1               5                   10

<210> SEQ ID NO 207
<211> LENGTH: 12
<212> TYPE: PRT
<213> ORGANISM: Artificial Sequence
<220> FEATURE:
<223> OTHER INFORMATION: Synthetic Peptide 3-35

<400> SEQUENCE: 207

Arg Met Pro Gly Asn Pro Gly Asn Pro Gly Arg Ser
1               5                   10

<210> SEQ ID NO 208
<211> LENGTH: 12
<212> TYPE: PRT
<213> ORGANISM: Artificial Sequence
<220> FEATURE:
<223> OTHER INFORMATION: Synthetic Peptide 3-36

<400> SEQUENCE: 208

Arg Met Pro Gly Met Pro Gly Thr Pro Gly Arg Ser
1               5                   10

<210> SEQ ID NO 209
<211> LENGTH: 12
<212> TYPE: PRT
<213> ORGANISM: Artificial Sequence
<220> FEATURE:
<223> OTHER INFORMATION: Synthetic Peptide 3-37

<400> SEQUENCE: 209

Arg Met Pro Gly Thr Pro Gly Met Pro Gly Arg Ser
1               5                   10

<210> SEQ ID NO 210
<211> LENGTH: 12
<212> TYPE: PRT
<213> ORGANISM: Artificial Sequence
<220> FEATURE:
<223> OTHER INFORMATION: Synthetic Peptide 3-38

<400> SEQUENCE: 210

Arg Met Pro Gly Thr Pro Gly Thr Pro Gly Arg Ser
1               5                   10

<210> SEQ ID NO 211
<211> LENGTH: 12
<212> TYPE: PRT
<213> ORGANISM: Artificial Sequence
<220> FEATURE:
<223> OTHER INFORMATION: Synthetic Peptide 3-39

<400> SEQUENCE: 211

Arg Met Pro Gly Met Pro Gly Leu Pro Gly Arg Ser
1               5                   10

```
<210> SEQ ID NO 212
<211> LENGTH: 12
<212> TYPE: PRT
<213> ORGANISM: Artificial Sequence
<220> FEATURE:
<223> OTHER INFORMATION: Synthetic Peptide 3-40

<400> SEQUENCE: 212

Arg Met Pro Gly Leu Pro Gly Met Pro Gly Arg Ser
1               5                   10

<210> SEQ ID NO 213
<211> LENGTH: 12
<212> TYPE: PRT
<213> ORGANISM: Artificial Sequence
<220> FEATURE:
<223> OTHER INFORMATION: Synthetic Peptide 3-41

<400> SEQUENCE: 213

Arg Met Pro Gly Leu Pro Gly Leu Pro Gly Arg Ser
1               5                   10

<210> SEQ ID NO 214
<211> LENGTH: 12
<212> TYPE: PRT
<213> ORGANISM: Artificial Sequence
<220> FEATURE:
<223> OTHER INFORMATION: Synthetic Peptide 3-42

<400> SEQUENCE: 214

Arg Thr Pro Gly Thr Pro Gly Gln Pro Gly Arg Ser
1               5                   10

<210> SEQ ID NO 215
<211> LENGTH: 12
<212> TYPE: PRT
<213> ORGANISM: Artificial Sequence
<220> FEATURE:
<223> OTHER INFORMATION: Synthetic Peptide 3-43

<400> SEQUENCE: 215

Arg Thr Pro Gly Gln Pro Gly Thr Pro Gly Arg Ser
1               5                   10

<210> SEQ ID NO 216
<211> LENGTH: 12
<212> TYPE: PRT
<213> ORGANISM: Artificial Sequence
<220> FEATURE:
<223> OTHER INFORMATION: Synthetic Peptide 3-44

<400> SEQUENCE: 216

Arg Thr Pro Gly Gln Pro Gly Gln Pro Gly Arg Ser
1               5                   10

<210> SEQ ID NO 217
<211> LENGTH: 12
<212> TYPE: PRT
<213> ORGANISM: Artificial Sequence
<220> FEATURE:
<223> OTHER INFORMATION: Synthetic Peptide 3-45

<400> SEQUENCE: 217

Arg Thr Pro Gly Thr Pro Gly Asn Pro Gly Arg Ser
1               5                   10

<210> SEQ ID NO 218
```

```
<211> LENGTH: 12
<212> TYPE: PRT
<213> ORGANISM: Artificial Sequence
<220> FEATURE:
<223> OTHER INFORMATION: Synthetic Peptide 3-46

<400> SEQUENCE: 218

Arg Thr Pro Gly Asn Pro Gly Thr Pro Gly Arg Ser
1               5                   10

<210> SEQ ID NO 219
<211> LENGTH: 12
<212> TYPE: PRT
<213> ORGANISM: Artificial Sequence
<220> FEATURE:
<223> OTHER INFORMATION: Synthetic Peptide 3-47

<400> SEQUENCE: 219

Arg Thr Pro Gly Asn Pro Gly Asn Pro Gly Arg Ser
1               5                   10

<210> SEQ ID NO 220
<211> LENGTH: 12
<212> TYPE: PRT
<213> ORGANISM: Artificial Sequence
<220> FEATURE:
<223> OTHER INFORMATION: Synthetic Peptide 3-48

<400> SEQUENCE: 220

Arg Thr Pro Gly Thr Pro Gly Met Pro Gly Arg Ser
1               5                   10

<210> SEQ ID NO 221
<211> LENGTH: 12
<212> TYPE: PRT
<213> ORGANISM: Artificial Sequence
<220> FEATURE:
<223> OTHER INFORMATION: Synthetic Peptide 3-49

<400> SEQUENCE: 221

Arg Thr Pro Gly Met Pro Gly Thr Pro Gly Arg Ser
1               5                   10

<210> SEQ ID NO 222
<211> LENGTH: 12
<212> TYPE: PRT
<213> ORGANISM: Artificial Sequence
<220> FEATURE:
<223> OTHER INFORMATION: Synthetic Peptide 3-50

<400> SEQUENCE: 222

Arg Thr Pro Gly Met Pro Gly Met Pro Gly Arg Ser
1               5                   10

<210> SEQ ID NO 223
<211> LENGTH: 12
<212> TYPE: PRT
<213> ORGANISM: Artificial Sequence
<220> FEATURE:
<223> OTHER INFORMATION: Synthetic Peptide 3-51

<400> SEQUENCE: 223

Arg Thr Pro Gly Thr Pro Gly Leu Pro Gly Arg Ser
1               5                   10

<210> SEQ ID NO 224
<211> LENGTH: 12
```

<212> TYPE: PRT
<213> ORGANISM: Artificial Sequence
<220> FEATURE:
<223> OTHER INFORMATION: Synthetic Peptide 3-52

<400> SEQUENCE: 224

Arg Thr Pro Gly Leu Pro Gly Thr Pro Gly Arg Ser
1               5                   10

<210> SEQ ID NO 225
<211> LENGTH: 12
<212> TYPE: PRT
<213> ORGANISM: Artificial Sequence
<220> FEATURE:
<223> OTHER INFORMATION: Synthetic Peptide 3-53

<400> SEQUENCE: 225

Arg Thr Pro Gly Leu Pro Gly Leu Pro Gly Arg Ser
1               5                   10

<210> SEQ ID NO 226
<211> LENGTH: 12
<212> TYPE: PRT
<213> ORGANISM: Artificial Sequence
<220> FEATURE:
<223> OTHER INFORMATION: Synthetic Peptide 3-54

<400> SEQUENCE: 226

Arg Leu Pro Gly Leu Pro Gly Gln Pro Gly Arg Ser
1               5                   10

<210> SEQ ID NO 227
<211> LENGTH: 12
<212> TYPE: PRT
<213> ORGANISM: Artificial Sequence
<220> FEATURE:
<223> OTHER INFORMATION: Synthetic Peptide 3-55

<400> SEQUENCE: 227

Arg Leu Pro Gly Gln Pro Gly Leu Pro Gly Arg Ser
1               5                   10

<210> SEQ ID NO 228
<211> LENGTH: 12
<212> TYPE: PRT
<213> ORGANISM: Artificial Sequence
<220> FEATURE:
<223> OTHER INFORMATION: Synthetic Peptide 3-56

<400> SEQUENCE: 228

Arg Leu Pro Gly Gln Pro Gly Gln Pro Gly Arg Ser
1               5                   10

<210> SEQ ID NO 229
<211> LENGTH: 12
<212> TYPE: PRT
<213> ORGANISM: Artificial Sequence
<220> FEATURE:
<223> OTHER INFORMATION: Synthetic Peptide 3-57

<400> SEQUENCE: 229

Arg Leu Pro Gly Leu Pro Gly Asn Pro Gly Arg Ser
1               5                   10

<210> SEQ ID NO 230
<211> LENGTH: 12
<212> TYPE: PRT

<213> ORGANISM: Artificial Sequence
<220> FEATURE:
<223> OTHER INFORMATION: Synthetic Peptide 3-58

<400> SEQUENCE: 230

Arg Leu Pro Gly Asn Pro Gly Leu Pro Gly Arg Ser
1               5                   10

<210> SEQ ID NO 231
<211> LENGTH: 12
<212> TYPE: PRT
<213> ORGANISM: Artificial Sequence
<220> FEATURE:
<223> OTHER INFORMATION: Synthetic Peptide 3-59

<400> SEQUENCE: 231

Arg Leu Pro Gly Asn Pro Gly Asn Pro Gly Arg Ser
1               5                   10

<210> SEQ ID NO 232
<211> LENGTH: 12
<212> TYPE: PRT
<213> ORGANISM: Artificial Sequence
<220> FEATURE:
<223> OTHER INFORMATION: Synthetic Peptide 3-60

<400> SEQUENCE: 232

Arg Leu Pro Gly Leu Pro Gly Met Pro Gly Arg Ser
1               5                   10

<210> SEQ ID NO 233
<211> LENGTH: 12
<212> TYPE: PRT
<213> ORGANISM: Artificial Sequence
<220> FEATURE:
<223> OTHER INFORMATION: Synthetic Peptide 3-61

<400> SEQUENCE: 233

Arg Leu Pro Gly Met Pro Gly Leu Pro Gly Arg Ser
1               5                   10

<210> SEQ ID NO 234
<211> LENGTH: 12
<212> TYPE: PRT
<213> ORGANISM: Artificial Sequence
<220> FEATURE:
<223> OTHER INFORMATION: Synthetic Peptide 3-62

<400> SEQUENCE: 234

Arg Leu Pro Gly Met Pro Gly Met Pro Gly Arg Ser
1               5                   10

<210> SEQ ID NO 235
<211> LENGTH: 12
<212> TYPE: PRT
<213> ORGANISM: Artificial Sequence
<220> FEATURE:
<223> OTHER INFORMATION: Synthetic Peptide 3-63

<400> SEQUENCE: 235

Arg Leu Pro Gly Leu Pro Gly Thr Pro Gly Arg Ser
1               5                   10

<210> SEQ ID NO 236
<211> LENGTH: 12
<212> TYPE: PRT
<213> ORGANISM: Artificial Sequence

```
<220> FEATURE:
<223> OTHER INFORMATION: Synthetic Peptide 3-64

<400> SEQUENCE: 236

Arg Leu Pro Gly Thr Pro Gly Leu Pro Gly Arg Ser
1               5                   10

<210> SEQ ID NO 237
<211> LENGTH: 12
<212> TYPE: PRT
<213> ORGANISM: Artificial Sequence
<220> FEATURE:
<223> OTHER INFORMATION: Synthetic Peptide 3-65

<400> SEQUENCE: 237

Arg Leu Pro Gly Thr Pro Gly Thr Pro Gly Arg Ser
1               5                   10

<210> SEQ ID NO 238
<211> LENGTH: 12
<212> TYPE: PRT
<213> ORGANISM: Artificial Sequence
<220> FEATURE:
<223> OTHER INFORMATION: Synthetic Peptide 3-66

<400> SEQUENCE: 238

Arg Gln Pro Gln Gln Pro Gln Gln Pro Gln Arg Ser
1               5                   10

<210> SEQ ID NO 239
<211> LENGTH: 12
<212> TYPE: PRT
<213> ORGANISM: Artificial Sequence
<220> FEATURE:
<223> OTHER INFORMATION: Synthetic Peptide 3-67

<400> SEQUENCE: 239

Arg Asn Pro Asn Asn Pro Asn Asn Pro Asn Arg Ser
1               5                   10

<210> SEQ ID NO 240
<211> LENGTH: 12
<212> TYPE: PRT
<213> ORGANISM: Artificial Sequence
<220> FEATURE:
<223> OTHER INFORMATION: Synthetic Peptide 3-68

<400> SEQUENCE: 240

Arg Met Pro Met Met Pro Met Met Pro Met Arg Ser
1               5                   10

<210> SEQ ID NO 241
<211> LENGTH: 12
<212> TYPE: PRT
<213> ORGANISM: Artificial Sequence
<220> FEATURE:
<223> OTHER INFORMATION: Synthetic Peptide 3-69

<400> SEQUENCE: 241

Arg Thr Pro Thr Thr Pro Thr Thr Pro Thr Arg Ser
1               5                   10

<210> SEQ ID NO 242
<211> LENGTH: 12
<212> TYPE: PRT
<213> ORGANISM: Artificial Sequence
<220> FEATURE:
```

```
<223> OTHER INFORMATION: Synthetic Peptide 3-70

<400> SEQUENCE: 242

Arg Leu Pro Leu Leu Pro Leu Leu Pro Leu Arg Ser
1               5                   10
```